United States Patent
Xia et al.

(10) Patent No.: US 9,634,265 B2
(45) Date of Patent: *Apr. 25, 2017

(54) ORGANIC ELECTROLUMINESCENT MATERIALS AND DEVICES

(71) Applicant: Universal Display Corporation, Ewing, NJ (US)

(72) Inventors: Chuanjun Xia, Lawrenceville, NJ (US); James Fiordeliso, Yardley, PA (US); Raymond Kwong, Fo Tan (HK)

(73) Assignee: Universal Display Corporation, Ewing, NJ (US)

( * ) Notice: Subject to any disclaimer, the term of this patent is extended or adjusted under 35 U.S.C. 154(b) by 874 days.

This patent is subject to a terminal disclaimer.

(21) Appl. No.: 13/960,264

(22) Filed: Aug. 6, 2013

(65) Prior Publication Data

US 2013/0320318 A1    Dec. 5, 2013

Related U.S. Application Data

(63) Continuation of application No. 12/768,068, filed on Apr. 27, 2010, now Pat. No. 8,557,400.

(60) Provisional application No. 61/173,346, filed on Apr. 28, 2009.

(51) Int. Cl.
| | |
|---|---|
| *H01L 51/54* | (2006.01) |
| *C09K 11/06* | (2006.01) |
| *H01L 51/00* | (2006.01) |
| *C07F 15/00* | (2006.01) |
| *H05B 33/14* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1007* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 8,557,400 B2 * | 10/2013 | Xia et al. ............. | C07F 15/0033 257/E51.044 |
| 8,592,586 B2 | 11/2013 | Molt et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Office Action issued for corresponding Taiwan Application No. 099113384 (translation).
Notice of Reasons for Rejection dated Apr. 7, 2014 issued for corresponding Japanese Patent Application No. 2012-508632.
Szalontai, Gabor et al., "Distinction of Tris(diimine)ruthenium(II) enantiomers chiral by virtue of helical chirality: Temperature-dependent deuterium NMR spectroscopy in partially oriented phases," Magn. Reson. Chem. 2006; 44: 1044-1050.
Kovacs, Margit et al., "Photophysics and electron transfer reactions of [Ru(LL)(CN)4] complexes," Radiation Physics and Chemistry 76 (2007) 1236-1243.

(Continued)

*Primary Examiner* — Marie R. Yamnitzky
(74) *Attorney, Agent, or Firm* — Duane Morris LLP

(57) ABSTRACT

Novel organic compounds comprising ligands with deuterium substitution are provided. In particular, the compound is an iridium complex comprising methyl-$d_3$ substituted ligands. The compounds may be used in organic light emitting devices to provide devices having improved color, efficiency and lifetime.

26 Claims, 4 Drawing Sheets

(56) References Cited

U.S. PATENT DOCUMENTS

| | | |
|---|---|---|
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0233433 A1 | 9/2008 | Igarashi et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0153045 A1 | 6/2009 | Kinoshita et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0295274 A1 | 12/2009 | Hwang et al. |
| 2011/0087026 A1 | 4/2011 | Molt et al. |
| 2011/0284799 A1 | 11/2011 | Stoessel et al. |

FOREIGN PATENT DOCUMENTS

| | | |
|---|---|---|
| EP | 2031037 | 3/2009 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 0247440 | 6/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006095951 | 9/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008014037 | 1/2008 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Connor, Joseph A. et al., "Solvent Influences on the Spectra of Tetracarbonyl (4,4'-disubstituted-2,2'-bipyridine) molybdenum Complexes," Inorganica Chimica Acta., 65 (1982) L1.

Japanese Patent Office, Notification of the First Office Action—English Version of Japanese Office Action regarding corresponding Japanese Application No. 2012-508632 issued Apr. 27, 2015, pp. 1-4.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al.,":Highly Efficient Phosphorescent Emission from Organic Electroluminescent Devices," Nature, vol. 395, 151-154, (1998).

Baldo et al.,"Very high-efficiency green organic light-emitting devices based on electrophosphorescence," Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1:15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett, 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett, 90:123509-1-123509-3 (2007).

Kido, Junji et al.,"1,2,4-Triazole Derivative as an Electron Transport Layer in Organic Electroluminescent Devices," Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylbory;)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al.,"A Novel Class of Phosphorescent Gold(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

III　　　　　　　　IV　　　　　　　　V

VI　　　　　　　　VII　　　　　　　　VIII

ORGANIC ELECTROLUMINESCENT MATERIALS AND DEVICES

This application is a continuation of co-pending U.S. patent application Ser. No. 12/768,068, filed Apr. 27, 2010, now U.S. Pat. No. 8,557,400 which claims priority to U.S. Provisional Application Ser. No. 61/173,346, filed Apr. 28, 2009, the entire disclosures of which are herein expressly incorporated by reference.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic compounds that may be advantageously used in organic light emitting devices. More particularly, the invention relates to novel methyl-d3 substituted iridium complexes and their use in OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

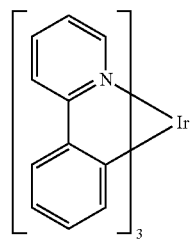

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound comprising a ligand having the structure:

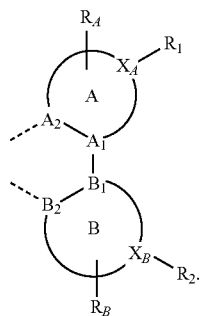

FORMULA I

A and B may independently represent a 5-membered or 6-membered aromatic or heteroaromatic ring. Preferably, A is selected from the group consisting of imidazole, pyrazole, triazole, oxazole, oxadiazole, pyridine, pyridazine, pyrimidine, pyrazine, and triazine. Preferably, B is selected from the group consisting of benzene, pyridine, furan, pyrrole, and thiophene. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked. $R_A$, $R_B$, $R_1$ and $R_2$ may be fused. The ligand is coordinated to a metal having an atomic weight greater than 40. Preferably, the metal is Ir.

In one aspect, the ligand has the structure:

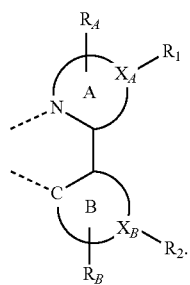

FORMULA Ia

In one aspect, $X_A$ and $X_B$ are independently C or N and when $X_A$ is N, $R_1$ is aryl. In another aspect, $X_A$ and $X_B$ are independently C or N and when $X_A$ is N, $R_1$ is phenyl further substituted with a group consisting of alkyl, alkoxy, amino, alkenyl, alkynyl, arylkyl, aryl, and heteroaryl and wherein the group includes at least one of CD, $CD_2$ or $CD_3$.

In one aspect, compounds are provided wherein at least one of the substituents of $R_A$ and $R_B$ is $CD_3$ attached directly to ring A, ring B, or a ring that is conjugated or fused to ring A or ring B.

In particular, compounds are provided comprising a ligand wherein the ligand is selected from the group consisting of:

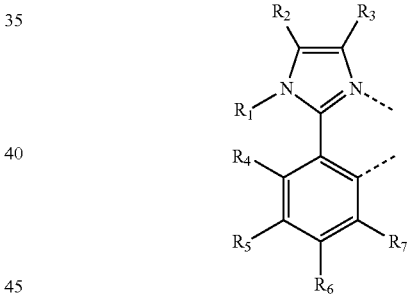

II

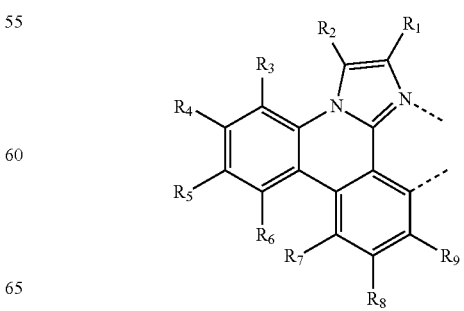

III

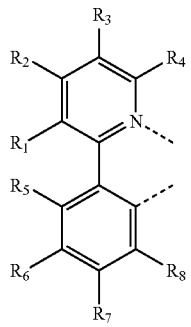

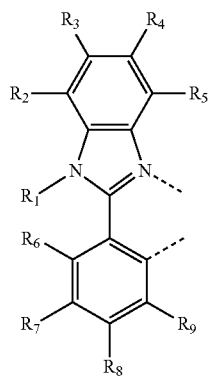

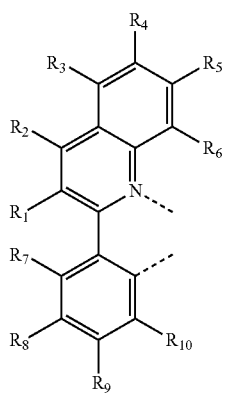

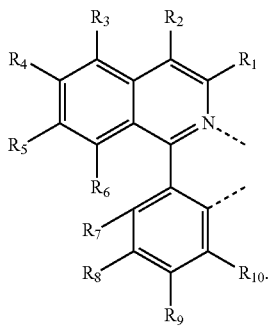

$R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ is $CD_3$.

In another aspect, compounds comprise a ligand selected from Formula II, III, IV, V, VI, and VII. $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ includes $CD_3$.

In yet another aspect, compounds are provided comprising a ligand selected from the group consisting of:

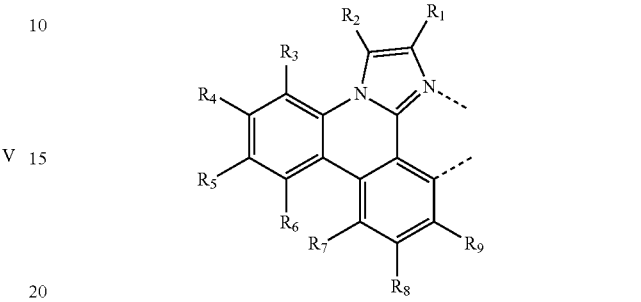

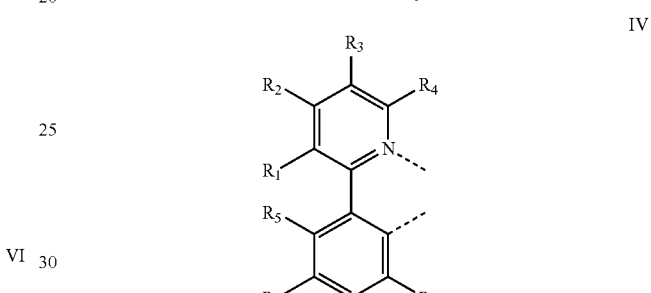

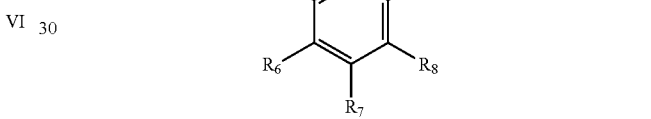

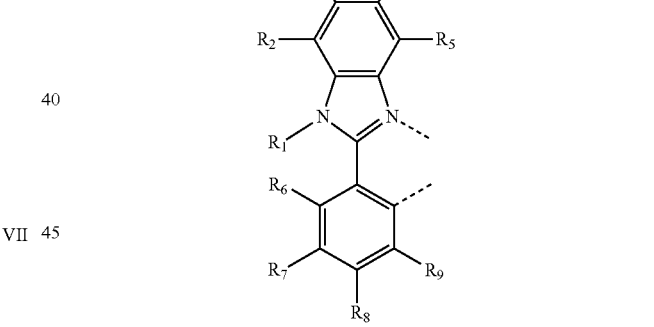

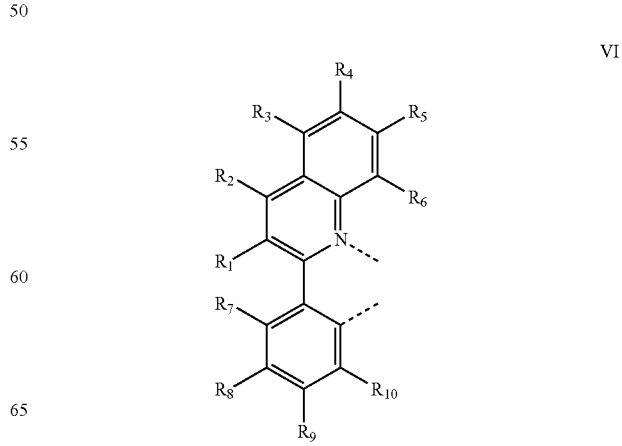

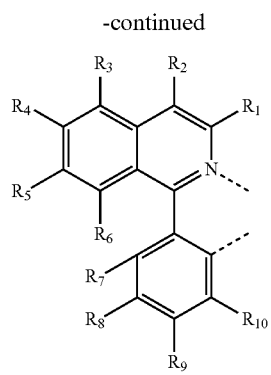

VII

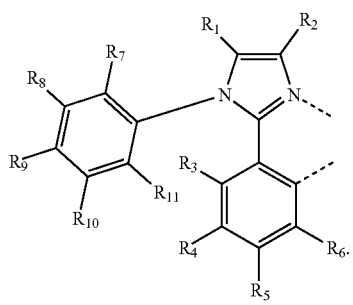

VIII $R_1$, $R_2$, $R_3$, $R_4$, $R_5$, $R_6$, $R_7$, $R_8$, $R_9$, $R_{10}$, and $R_{11}$ are independently selected from the group consisting of hydrogen, alkyl, alkoxy, amino, alkenyl, alkynyl, arylkyl, aryl, and heteroaryl. $R_1$, $R_2$, $R_3$, $R_4$, $R_5$, $R_6$, $R_7$, $R_8$, $R_9$, $R_{10}$, and $R_{11}$ may be linked. $R_1$, $R_2$, $R_3$, $R_4$, $R_5$, $R_6$, $R_7$, $R_8$, $R_9$, $R_{10}$, and $R_{11}$ may be fused. At least one of $R_1$, $R_2$, $R_3$, $R_4$, $R_5$, $R_6$, $R_7$, $R_8$, $R_9$, $R_{10}$, and $R_{11}$ includes an alkyl group that includes CD, $CD_2$, or $CD_3$.

Specific examples of methyl-deuterium substituted (also referred to herein as methyl-d3 or $CD_3$) iridium complexes are provided, and include compounds selected from the group consisting of Compounds 2-42. In one aspect, compounds are provided wherein the compound comprises a ligand having Formula II, for example, Compounds 2-4. In another aspect, compounds are provided wherein the compound comprises a ligand having Formula III, for example, Compounds 5-9. In yet another aspect, Compounds are provided wherein the compound comprises a ligand having Formula IV, for example, Compounds 10-14 and 27-40. In yet another aspect, Compounds are provided wherein the compound comprises a ligand having Formula V, for example, Compounds 15-19. In yet another aspect, Compounds are provided wherein the compound comprises a ligand having Formula VI, for example, Compounds 20-23. In yet another aspect, Compounds are provided wherein the compound comprises a ligand having Formula VII, for example, Compounds 24-26, 41, and 42.

Additional specific example of deuterium substituted compounds include compounds selected from the group consisting of Compound 43-Compound 67, Compound 69-Compound 82. In one aspect, compounds are provided wherein the compound comprises a ligand having Formula III, for example, Compounds 58, 59, 69-70 and 75-77. In another aspect, compounds are provided wherein the compound comprises a ligand having Formula IV, for example, Compounds 43-52, 62-67, and 80-82. In yet another aspect, compounds are provided wherein the compound comprises a ligand having Formula V, for example, Compounds 55-57, 73 and 74. In a further aspect, compounds are provided wherein the compound comprises a ligand having Formula VI, for example, Compounds 60, 61, 78 and 79. In yet another aspect, compounds are provided wherein the compound comprises a ligand having Formula VIII, for example, Compounds 53, 54, 71 and 72.

In one aspect, homoleptic compounds are provided. In particular, compounds are provided wherein the ligand having FORMULA I is in a ligand in a homoleptic compound. In another aspect, heteroleptic compounds are provided. In particular compounds are provided wherein the ligand having FORMULA I is a ligand in a heteroleptic compound.

An organic light emitting device is also provided. The device may include an anode, a cathode, and an organic emissive layer disposed between the anode and the cathode. The organic layer further comprises a ligand having the structure of FORMULA I, as described above.

A and B may independently represent a 5-membered or 6-membered aromatic or heteroaromatic ring. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked. $R_A$, $R_B$, $R_1$ and $R_2$ may be fused. The ligand is coordinated to a metal having an atomic weight greater than 40.

In one aspect, $X_A$ and $X_B$ are independently C or N and when $X_A$ is N, $R_1$ is aryl. In another aspect, $X_A$ and $X_B$ are independently C or N and when $X_A$ is N, $R_1$ is phenyl further substituted with a group consisting of alkyl, alkoxy, amino, alkenyl, alkynyl, arylkyl, aryl, and heteroaryl and wherein the group includes at least one of CD, $CD_2$ or $CD_3$.

Selections for the aromatic rings, metal, and substituents described as preferred for compounds comprising a ligand having FORMULA I are also preferred for use in a device that includes a compound comprising a ligand having FORMULA I. These selections include those for metal M, rings A and B, and substituents $R_A$, $R_B$, $A_1$, $A_2$, $B_1$, $B_2$, $R_1$, and $R_2$.

Preferably, at least one of the substituents of $R_A$ and $R_B$ is $CD_3$ attached directly to ring A, ring B, or a ring that is conjugated or fused to ring A or ring B.

Preferably, the metal is Ir.

Preferably, A is selected from the group consisting of imidazole, pyrazole, triazole, oxazole, oxadiazole, pyridine, pyridazine, pyrimidine, pyrazine, and triazine. Preferably, B is selected from the group consisting of benzene, pyridine, furan, pyrrole, and thiophene.

In particular, the organic layer of the device may comprise a compound having a ligand selected from the group consisting of Formula II-VII, wherein $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ is $CD_3$. Preferably, the organic layer comprises a compound selected from the group consisting of Compounds 2-42.

Additionally, the organic layer of the device may comprise a compound having a ligand selected from the group consisting of Formula II-VII, wherein $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ includes $CD_3$.

Moreover, the organic layer of the device may comprise a compound having a ligand selected from the group consisting of Formula III-VIII. $R_1$, $R_2$, $R_3$, $R_4$, $R_5$, $R_6$, $R_7$, $R_8$, $R_9$, $R_{10}$, and $R_{11}$ are independently selected from the group consisting of hydrogen, alkyl, alkoxy, amino, alkenyl, alkynyl, arylkyl, aryl, and heteroaryl. $R_1$, $R_2$, $R_3$, $R_4$, $R_5$, $R_6$, $R_7$, $R_8$, $R_9$, $R_{10}$, and $R_{11}$ may be linked. $R_1$, $R_2$, $R_3$, $R_4$, $R_5$, $R_6$, $R_7$, $R_8$, $R_9$, $R_{10}$, and $R_{11}$ may be fused. At least one of $R_1$, $R_2$, $R_3$, $R_4$, $R_5$, $R_6$, $R_7$, $R_8$, $R_9$, $R_{10}$, and $R_{11}$ includes an alkyl group that includes CD, $CD_2$, or $CD_3$. Preferably, the organic layer comprises a compound selected from the group consisting of Compounds 43-82.

In one aspect, the organic layer is an emissive layer containing a compound provided herein wherein the compound is an emitting dopant. The organic layer may further comprise a host. Preferably, the host has the formula:

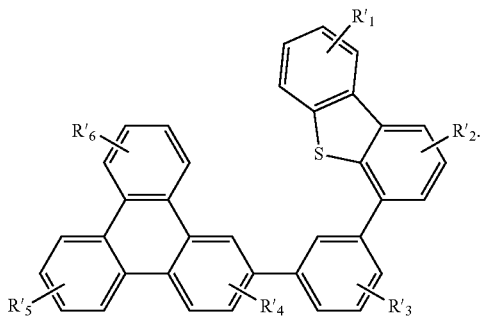

$R'_1$, $R'_2$, $R'_3$, $R'_4$, $R'_5$, and $R'_6$ may represent mono, di, tri, or tetra substitutions; and each of $R'_1$, $R'_2$, $R'_3$, $R'_4$, $R'_5$, and $R'_6$ is independently selected from the group consisting of hydrogen, alkyl and aryl. More preferably, the host is H1.

A consumer product comprising a device is also provided. The device comprises an anode, a cathode, and an organic layer disposed between the anode and the cathode. The organic layer comprises a compound containing a ligand having the structure of FORMULA I, as described above.

A and B may independently represent a 5-membered or 6-membered aromatic or heteroaromatic ring. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked. $R_A$, $R_B$, $R_1$ and $R_2$ may be fused. The ligand is coordinated to a metal having an atomic weight greater than 40.

Selections for the aromatic rings, metal, and substituents described as preferred for compounds comprising a ligand having FORMULA I are also preferred for use in a consumer product comprising device that includes a compound comprising a ligand having FORMULA I. These selections include those for metal M, rings A and B, and substituents $R_A$, $R_B$, $A_1$, $A_2$, $B_1$, $B_2$, $R_1$, and $R_2$.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
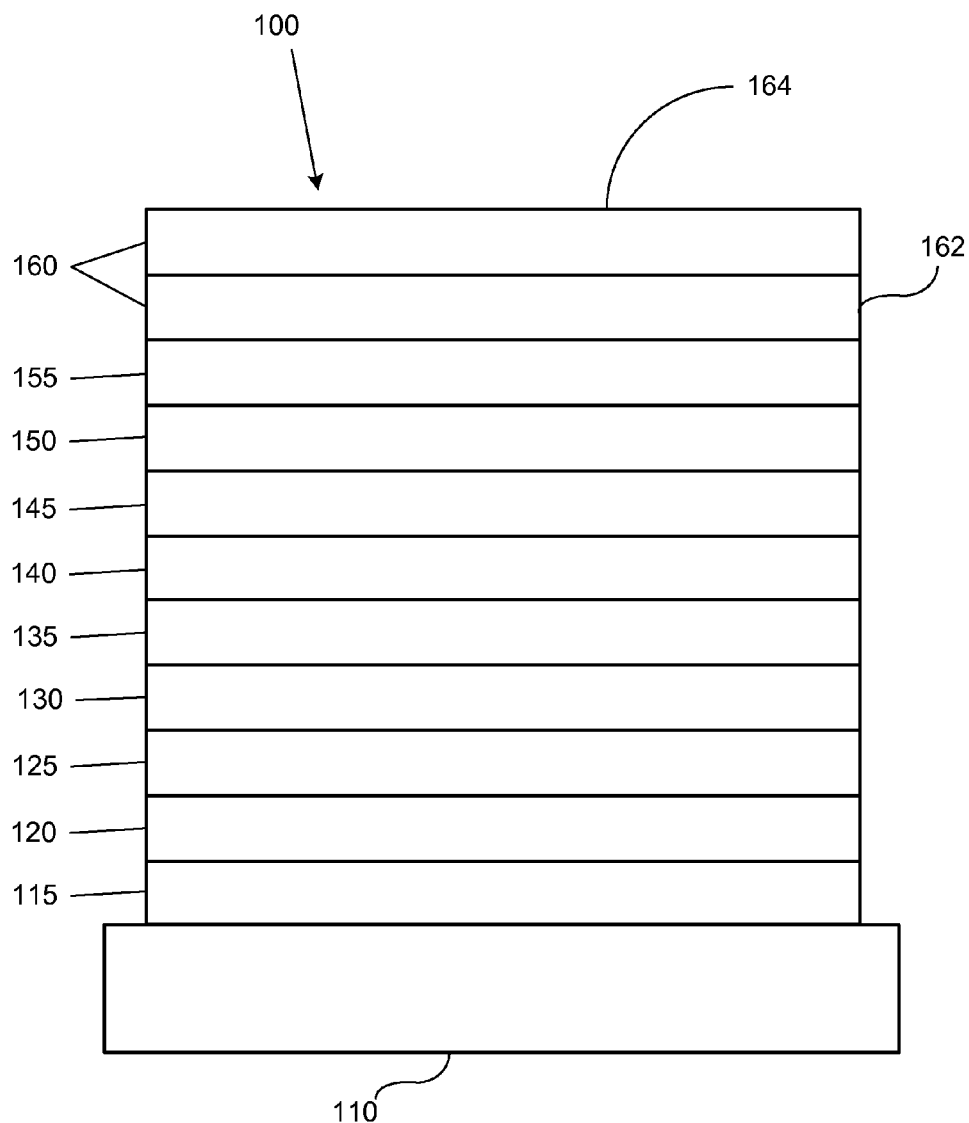
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
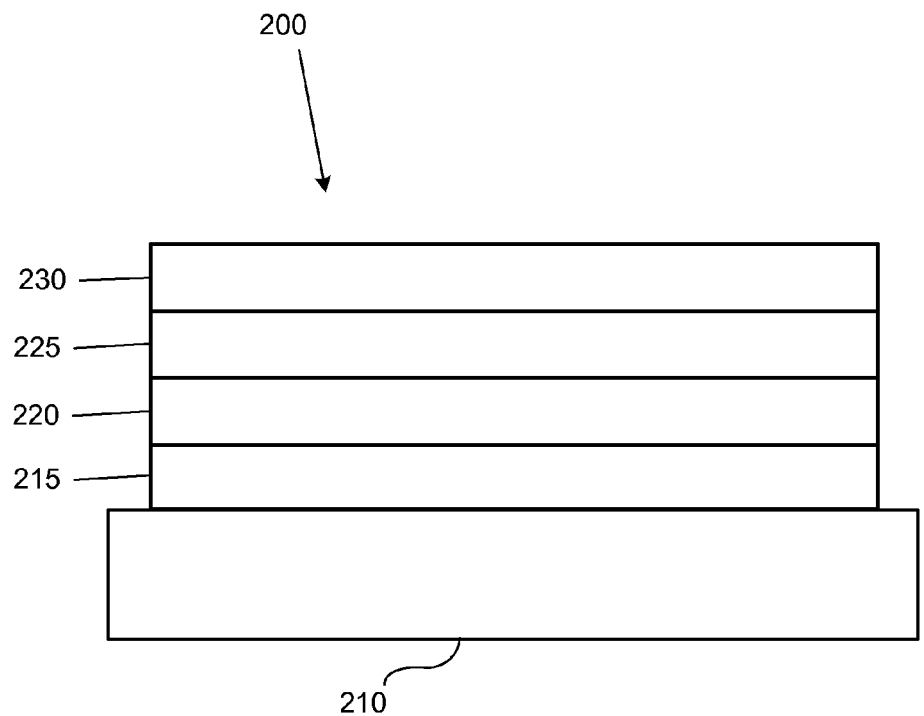
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968 which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

As used herein, the terms alkyl, aryl, and heteroaryl also include deuterium in place of hydrogen. For example, alkyl may include $CH_3$ or $CD_3$, and $CH_2CH_3$ or $CH_2CD_3$. Similarly, aryl and heteroaryl may include aromatic groups substituted with deuterium rather than hydrogen.

Replacing hydrogen with its isotope deuterium in iridium complexes has been reported in the literature (see, for example, U.S. Pub. No. 2008/0194853 and U.S. Pat. No. 6,699,599). Notably, deuterium atom substitution directly on the ring does not seem to provide color tuning. In particular, the inventors are not aware of any reports of a change in the emission profile of compounds substituted with deuterium atoms.

$CD_3$ substitution in a host material has also been reported (see, WO2008029670). However, the emission profile of an emitting dopant is an important property of the compound and substitution of a host material cannot provide any information regarding color tuning In particular, the effect of deuterium substitution of the photoluminescence spectra (e.g., color tuning properties) cannot be assessed when the compound being modified is a host material rather than an emissive material, as provided herein. Therefore, emissive compounds having the beneficial properties of methyl substitution (i.e., color tuning, improved quantum efficiency and improved lifetime) as well as improved stability associated with deuterium may be desirable.

Methyl substitution of metal complexes has been shown to be useful for tuning the photophysical and electroluminescence properties of a compound. For example, methyl substitution at certain positions may be beneficial for its ability to improve the quantum efficiency, line shape, and improve the lifetime of an OLED.

Figure 3:
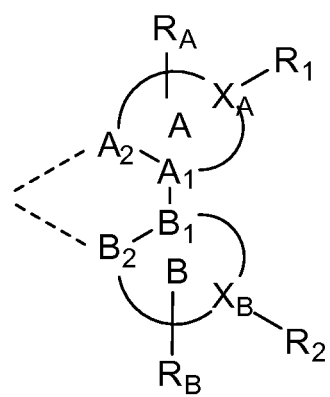
FIG. 3 shows the general structure of a ligand containing deuterium substitution.
Figure 4:
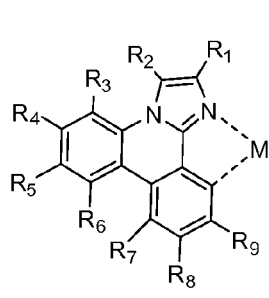
FIG. 4 shows exemplary methyl-d3 substituted ligands.
Figure 4:
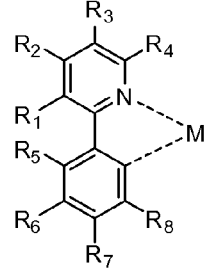
Figure 4:
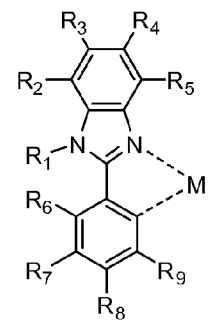
Figure 4:
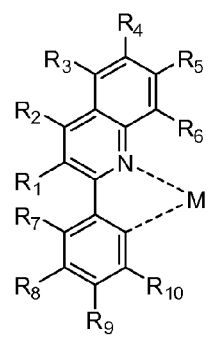
Figure 4:
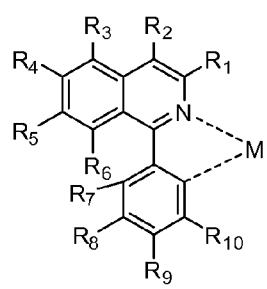
Figure 4:
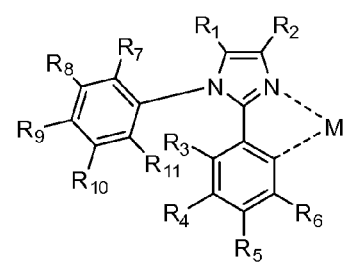

Novel compounds are provided herein, the compounds comprising a ligand having a methyl-d3 substituent (illustrated in FIG. 3). In addition, particular ligands containing methyl-d3 substitution are also provided (illustrated in FIG. 4). Notably, both improved photoluminescence and improved device efficiency may be provided with the compounds disclosed.

Compounds provided herein comprise a ligand having a methyl-d3 substitution. These compounds may be advantageously used in an OLED to provide devices having improved efficiency, long lifetime and improved color (e.g., color tuning). Without being bound by theory, it is believed that the $CD_3$ substituent may improve stability because of the strong C-D bond. The strength of the C-D bond is greater than that of the C—H bond, as discussed above. Additionally, the smaller van der Waals radius of deuterium may translate into a less steric substituent (e.g., less twist on an aromatic ring containing a $CD_3$ substituent at the ortho position rather than a $CH_3$ substituent) and thus improved conjugation in a system having $CD_3$ substitution. Further, the reaction rate of a chemical process involving the C-D bond present in methyl-d3 may be slower due to the kinetic isotope effect. If the chemical degradation of an emissive compound involved breaking the methyl C—H bond, then the stronger C-D bond may improve the stability of the compound.

Methyl is the most simple alkyl substitution added as a modification to a compound. It may be a very important substitution group to modify the properties of both hosts and emitters in an OLED. Methyl can affect the packing properties in the solid state (i.e. sublimation property and charge transporting property), modify photophysical properties, and affect device stability. Methyl groups have been introduced to change the properties of tris(2-phenylpyridine)iridium (III) family. For example, the devices with tris(3-methyl-2-phenylpyridine)iridium(III) as an emitter have better stability than those devices with tris(2-phenylpyridine)iridium (III) as an emitter. In addition, the emission peak of tris(3-methyl-2-phenylpyridine)iridium(III) is red shifted about 10 nm. The evaporation temperature of tris(3-methyl-2-phenylpyridine)iridium (III) is also about 20 degrees lower than tris(2-phenylpyridine)iridium(III).

On the other hand, methyl is also considered reactive because of the benzylic protons. Without being bound by theory, the hydrogen atoms present in the methyl group may be especially reactive and thus may be the site of chemical degradation in the emissive compound. Further, it is well accepted in the field that during OLED operation the dopant compounds become oxidized. In the oxidized state, the benzylic position may become the weakest position to undergo further chemical degradation. The proposed mechanism may be more relevant when the emitting dopant is used with certain hosts, such as triphenylene/DBT hybrid materials, and less relevant with other hosts, such as Balq. Therefore, replacing the hydrogen atoms in the methyl group with deuterium atoms (methyl-d3) may stabilize the emissive compound.

It is believed that deuterium substitution can improve efficiency and stability because the atomic mass of deuterium is twice as great as that of hydrogen, which results in lower zero point energy and lower vibration energy level. Additionally, the chemical bond lengths and bond angles involving deuterium are different than those involving hydrogen. In particular, the van der Vaals radius of deuterium is smaller than that of hydrogen, because of the smaller stretching amplitude of the C-D bond compared to the C—H bond. Generally, the C-D bond is shorter and stronger than the C—H bond. Therefore, $CD_3$ substitution may provide the same color tuning and all of the advantages associated with increased bond strength (i.e., improved efficiency and lifetime).

As discussed above, deuterium substitution provides many benefits, e.g., increased efficiency and lifetime. Therefore, compounds comprising a ligand having deuterium substitution may be advantageously used in organic light emitting devices. Such compounds include, for example, compounds comprising a ligand having deuterium within an alkyl chain, e.g., $C(D)(H)CH_3$, $CD_2CH_3$ and $CH_2CD_2CH_3$, as well as deuterium at the end of an alkyl chain, e.g., $CD_3$.

Novel compounds are provided herein, the compounds comprise a ligand having the structure:

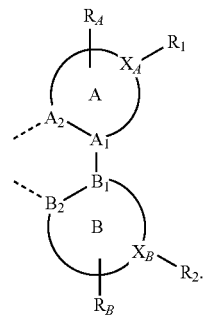

FORMULA I

A and B may independently represent a 5-membered or 6-membered aromatic or heteroaromatic ring. Preferably, A is selected from the group consisting of imidazole, pyrazole, triazole, oxazole, oxadiazole, pyridine, pyridazine, pyrimidine, pyrazine, and triazine. Preferably, B is selected from the group consisting of benzene, pyridine, furan, pyrrole, and thiophene. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked.

$R_A$, $R_B$, $R_1$ and $R_2$ may be fused. The ligand is coordinated to a metal having an atomic weight greater than 40. Preferably, the metal is Ir.

In one aspect, the ligand has the structure:

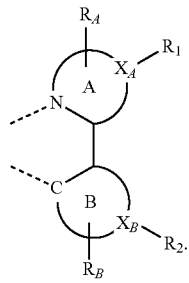

FORMULA Ia

In one aspect, $X_A$ and $X_B$ are independently C or N and when $X_A$ is N, $R_1$ is aryl. In another aspect, $X_A$ and $X_B$ are independently C or N and when $X_A$ is N, $R_1$ is phenyl further substituted with a group consisting of alkyl, alkoxy, amino, alkenyl, alkynyl, arylkyl, aryl, and heteroaryl and wherein the group includes at least one of CD, $CD_2$ or $CD_3$.

In one aspect, compounds are provided wherein at least 1 of the substituents of $R_A$ and $R_B$ is $CD_3$ attached directly to ring A, ring B, or a ring conjugated or fused to ring A or ring B.

As discussed above, the substituents $R_A$ and $R_B$ may be fused to ring A and/or ring B. The substituents $R_A$ and $R_B$ may be any substituents, including substituents that are linked, fused to ring A and/or ring B or not fused to ring A and/or ring B.

In particular, compounds are provided comprising a ligand wherein the ligand is selected from the group consisting of:

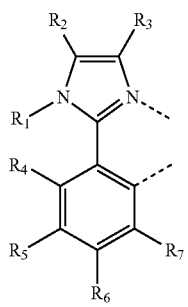

II

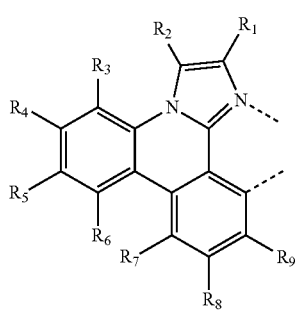

III

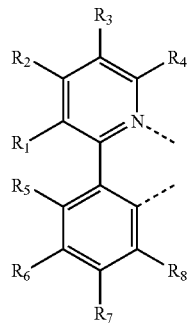

IV

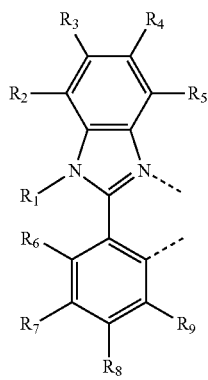

V

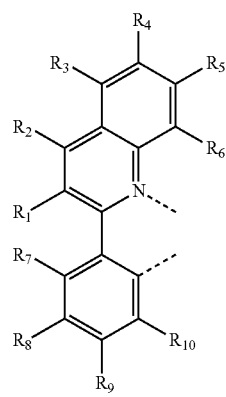

VI

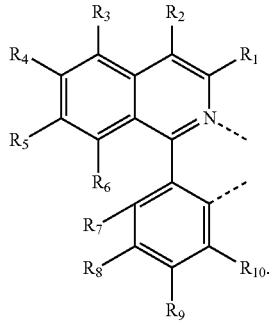

VII $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl; and at least one of $R_1$, $R_2$, $R_3$, $R_4$, $R_5$, $R_6$, $R_7$, $R_8$, $R_9$, and $R_{10}$ is $CD_3$.

Additionally, compounds are provided comprising a ligand wherein the ligand is selected from the group consisting of:

II
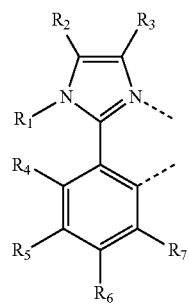
III
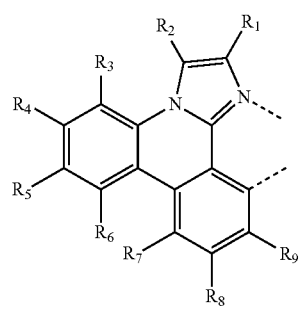
IV
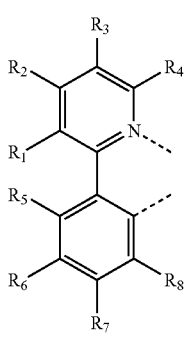
V
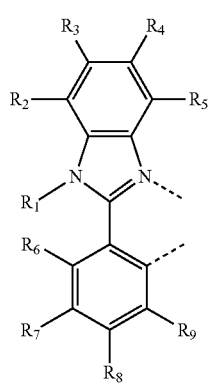
VI
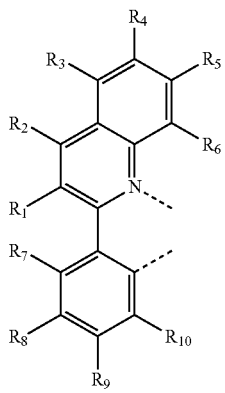
VII
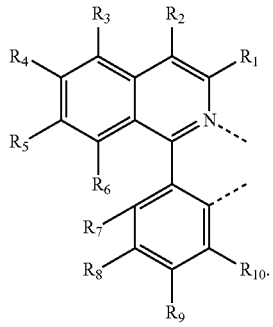
$R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl; and at least one of $R_1$, $R_2$, $R_3$, $R_4$, $R_5$, $R_6$, $R_7$, $R_8$, $R_9$, and $R_{10}$ includes $CD_3$.
Compounds comprising a ligand selected from the group consisting of:
III
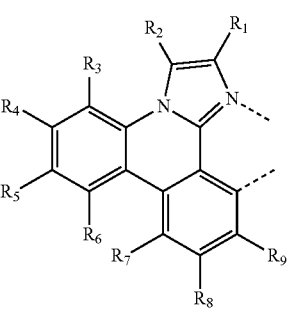
IV
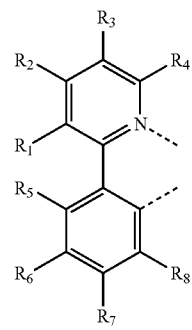

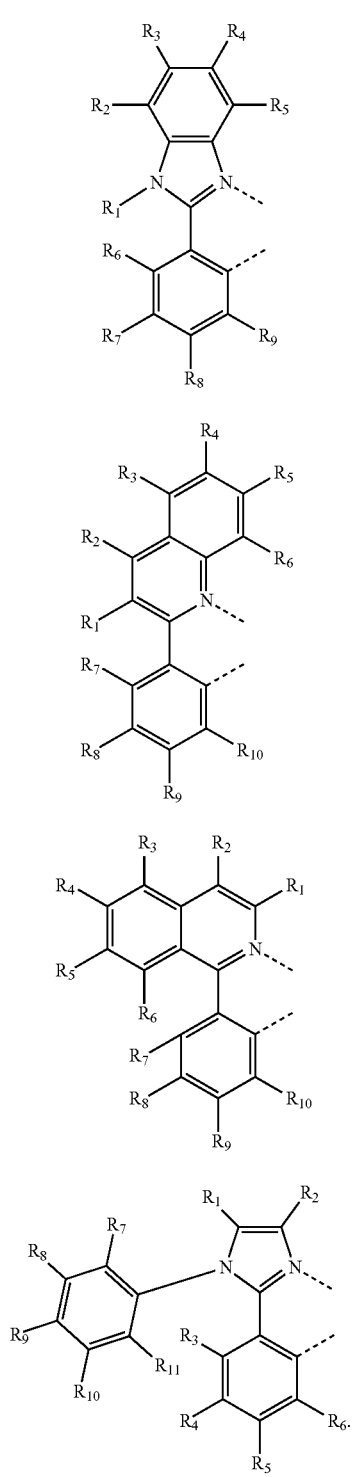

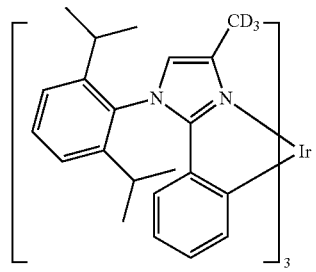
Compound 2

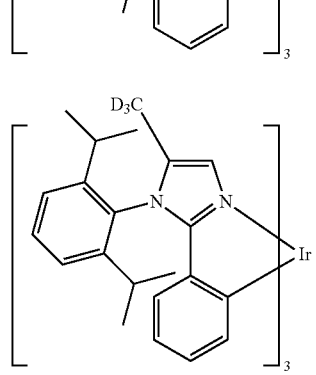
Compound 3

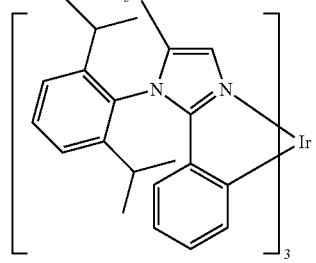
Compound 4

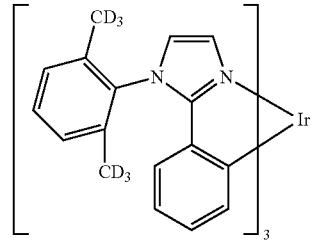
Compound 5

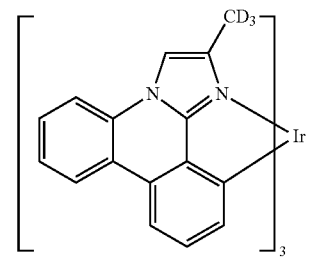
Compound 6

Specific examples of methyl-d3 substituted iridium complexes are provided, including compounds selected from the group consisting of:

$R_1$, $R_2$, $R_3$, $R_4$, $R_5$, $R_6$, $R_7$, $R_8$, $R_9$, $R_{10}$, and $R_{11}$ are independently selected from the group consisting of hydrogen, alkyl, alkoxy, amino, alkenyl, alkynyl, arylkyl, aryl, and heteroaryl; and $R_1$, $R_2$, $R_3$, $R_4$, $R_5$, $R_6$, $R_7$, $R_8$, $R_9$, $R_{10}$, and $R_{11}$ may be linked. $R_1$, $R_2$, $R_3$, $R_4$, $R_5$, $R_6$, $R_7$, $R_8$, $R_9$, $R_{10}$, and $R_{11}$ may be fused. At least one of $R_1$, $R_2$, $R_3$, $R_4$, $R_5$, $R_6$, $R_7$, $R_8$, $R_9$, $R_{10}$, and $R_{11}$ includes an alkyl group that includes CD, $CD_2$, or $CD_3$.

-continued
Compound 7
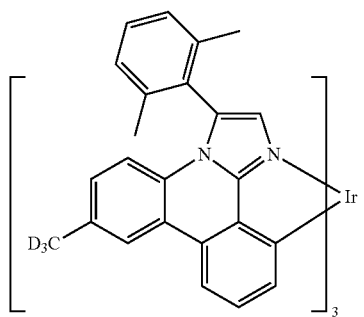
Compound 8
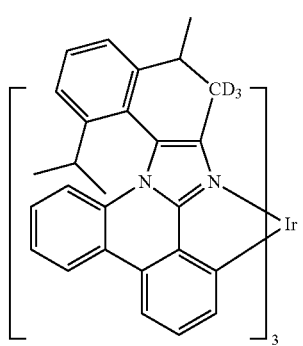
Compound 9
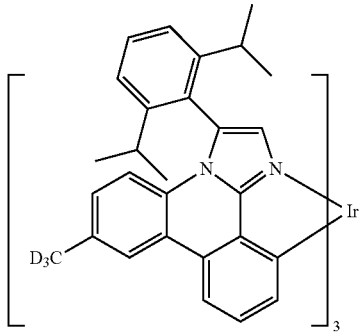
Compound 10
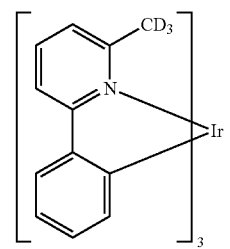
Compound 11
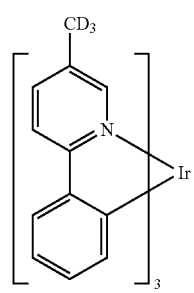
-continued
Compound 12
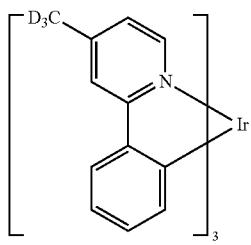
Compound 13
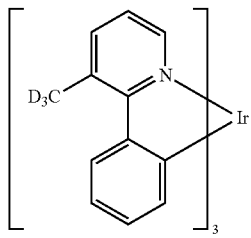
Compound 14
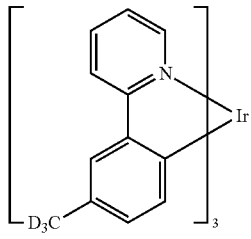
Compound 15
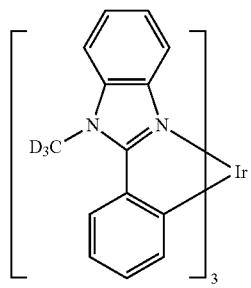
Compound 16
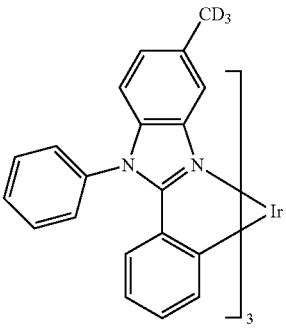

Compound 17
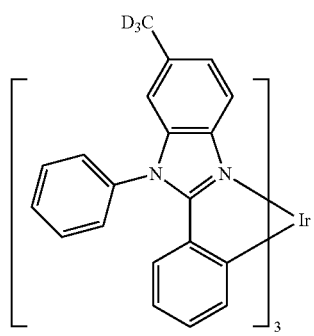
Compound 18
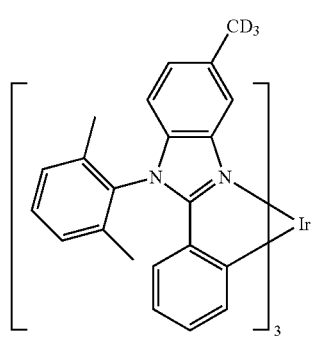
Compound 19
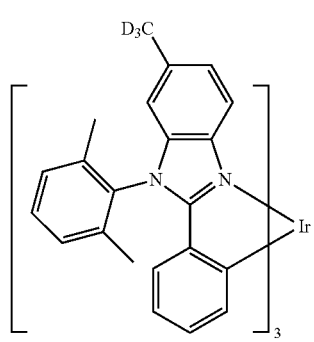
Compound 20
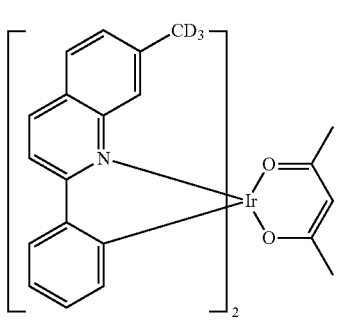
Compound 21
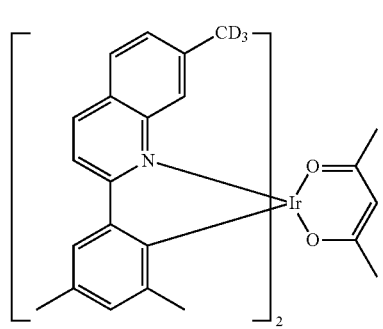
Compound 22
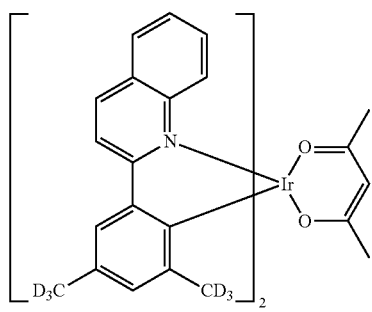
Compound 23
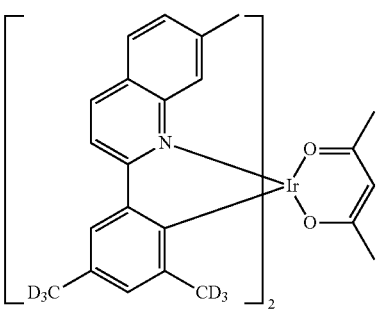
Compound 24
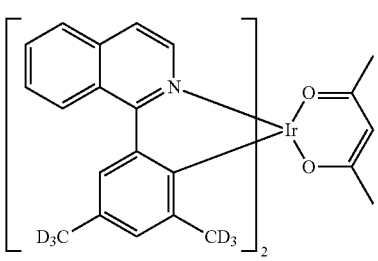
Compound 25
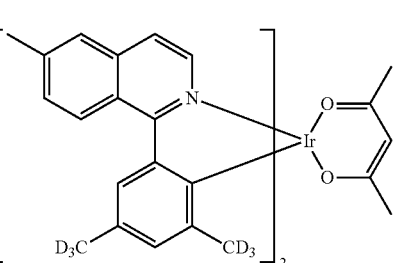
Compound 26
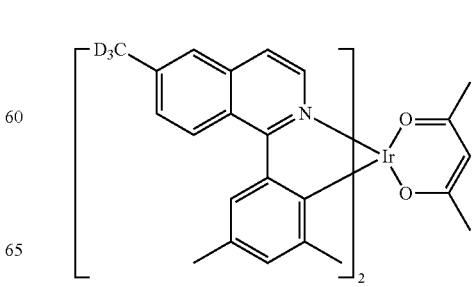

Compound 27
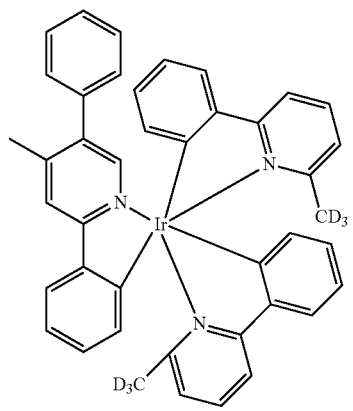
Compound 28
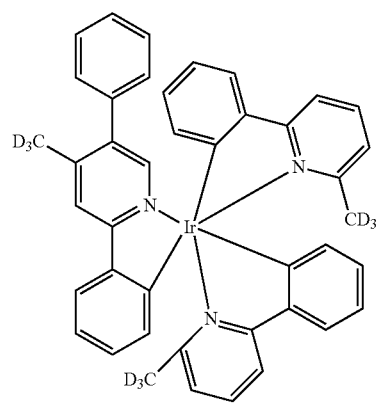
Compound 29
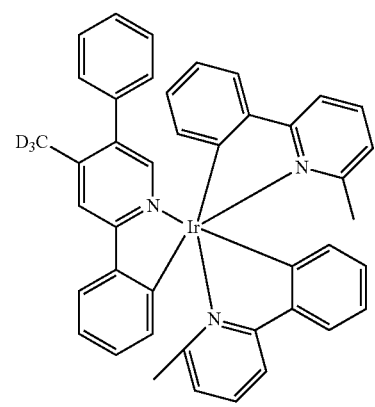
Compound 30
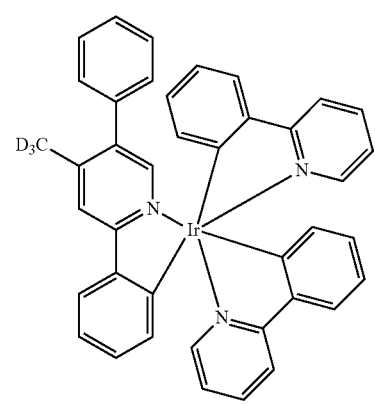
Compound 31
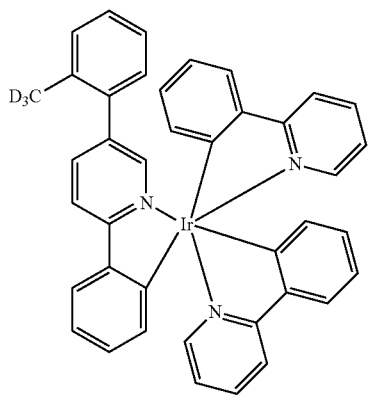
Compound 32
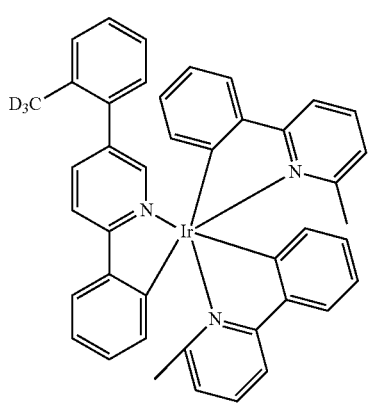
Compound 33
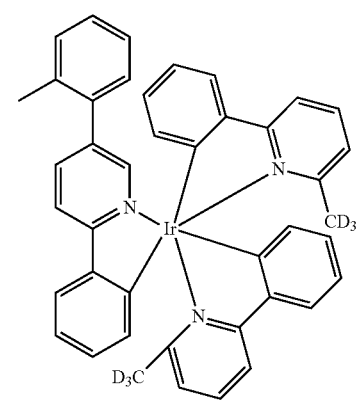
Compound 34
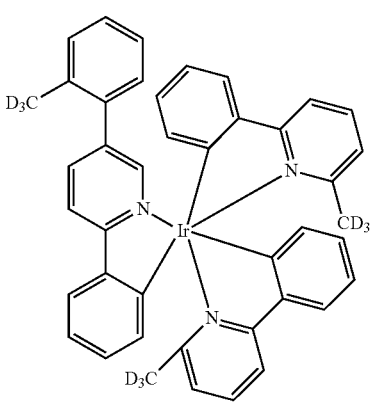

Compound 35
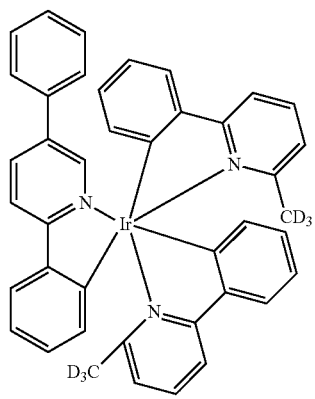
Compound 36
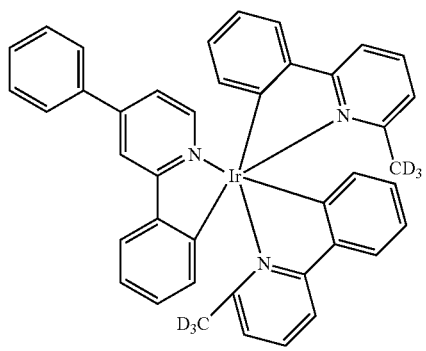
Compound 37
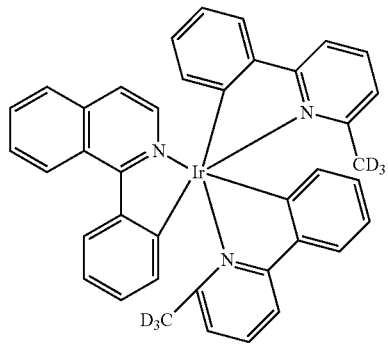
Compound 38
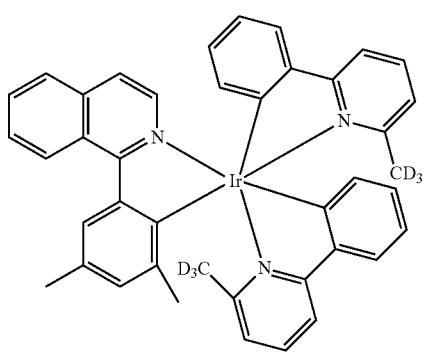
Compound 39
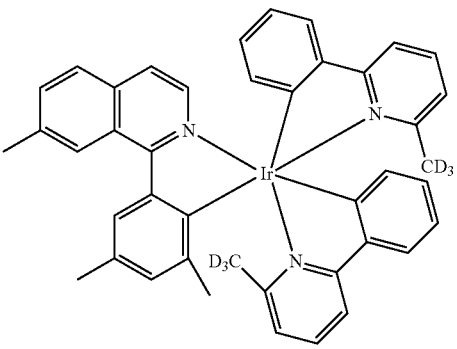
Compound 40
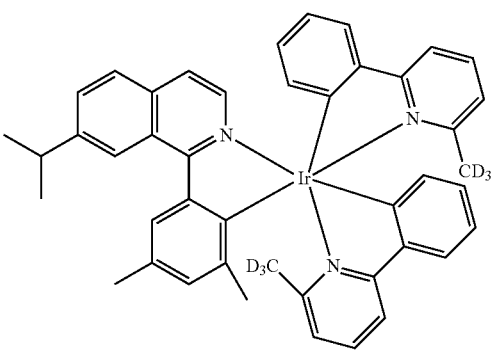
Compound 41
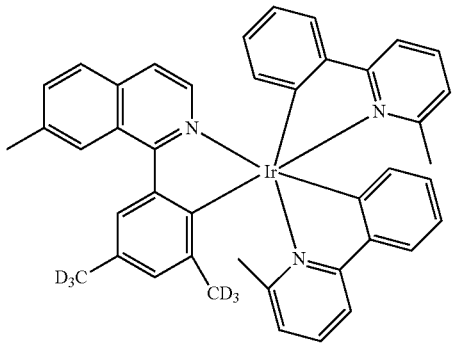
Compound 42
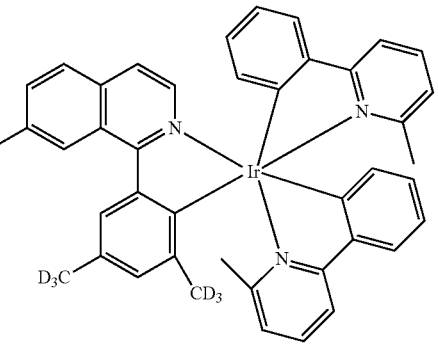
Additional specific examples of deuterium substituted iridium complexes are provided, including compounds selected from the group consisting of:

Compound 43
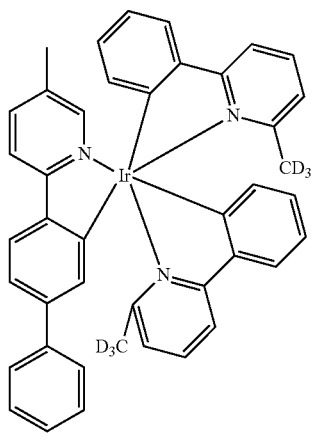
Compound 46
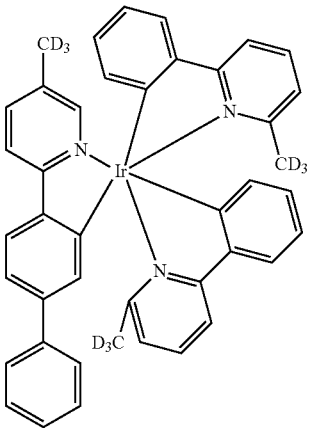
Compound 44
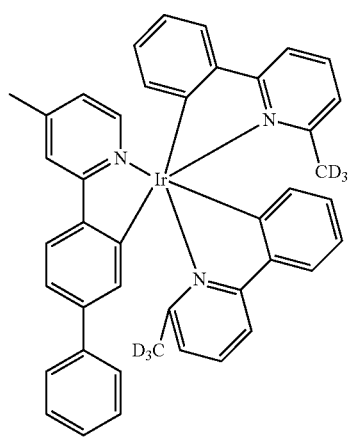
Compound 47
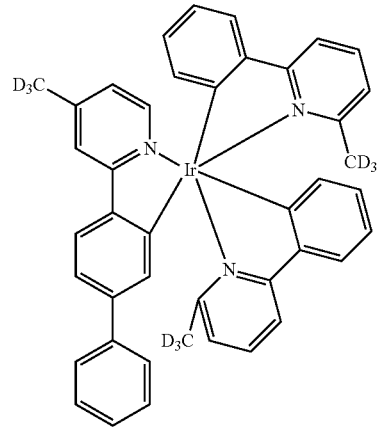
Compound 45
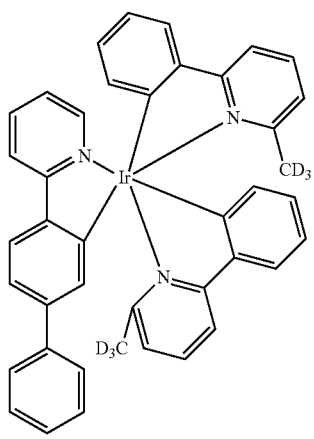
Compound 48
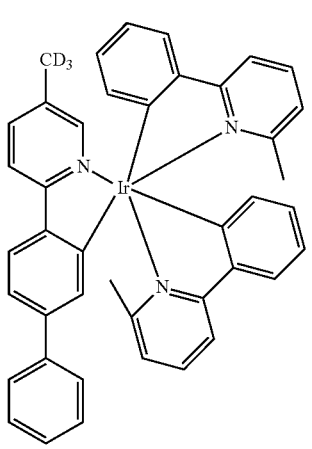

Compound 49
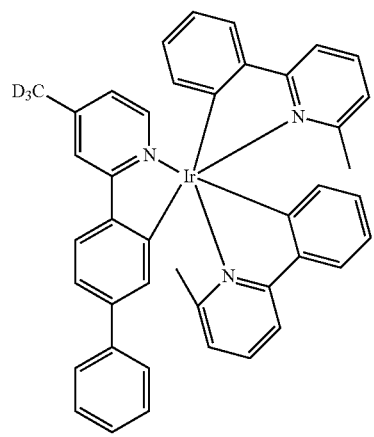
Compound 50
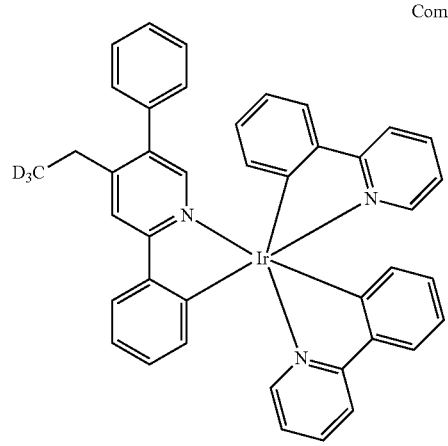
Compound 51
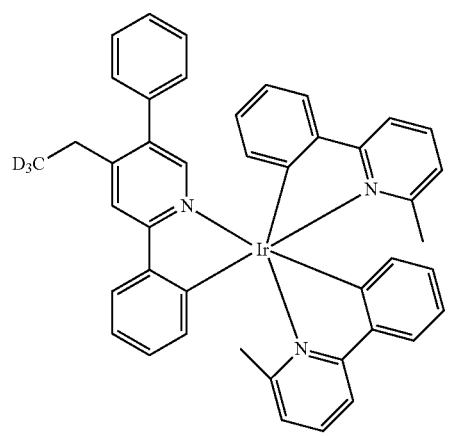
Compound 52
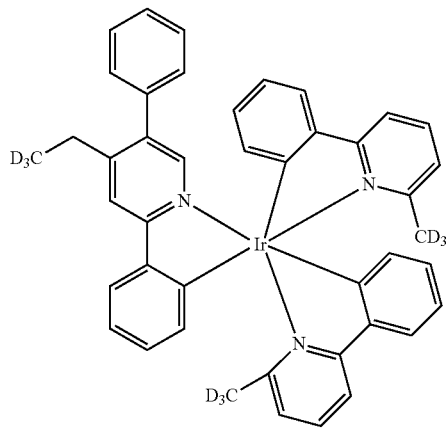
Compound 53
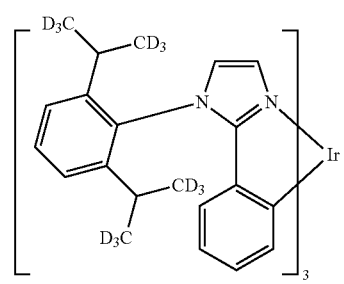
Compound 54
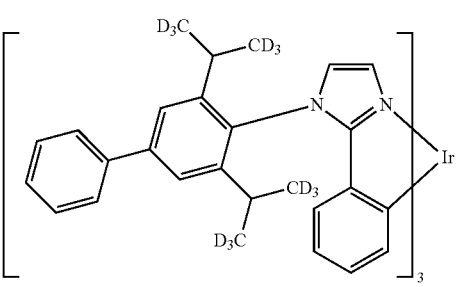
Compound 55
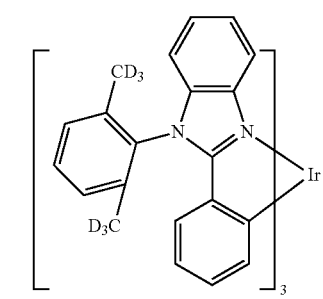
Compound 56
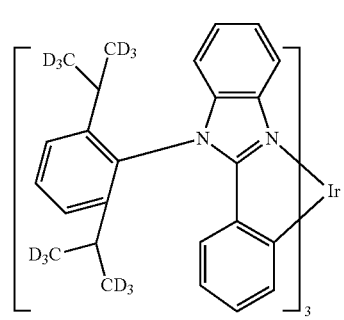

Compound 57
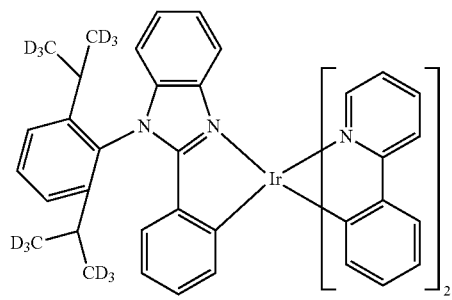
Compound 58
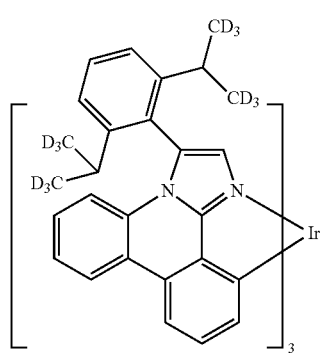
Compound 59
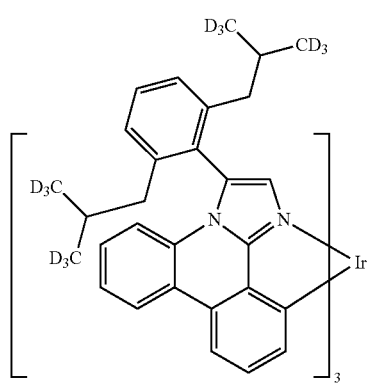
Compound 60
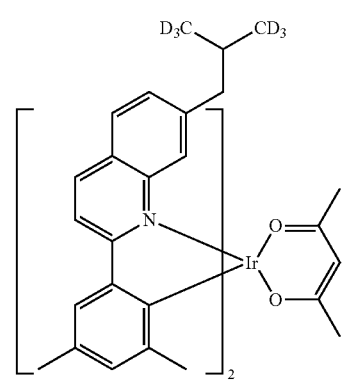
Compound 61
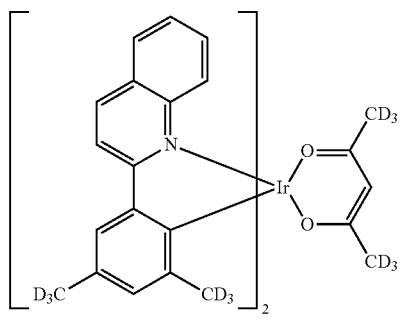
Compound 62
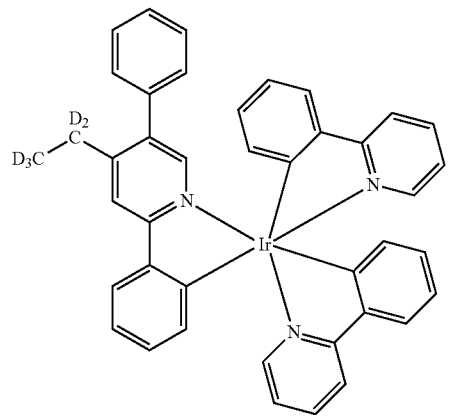
Compound 63
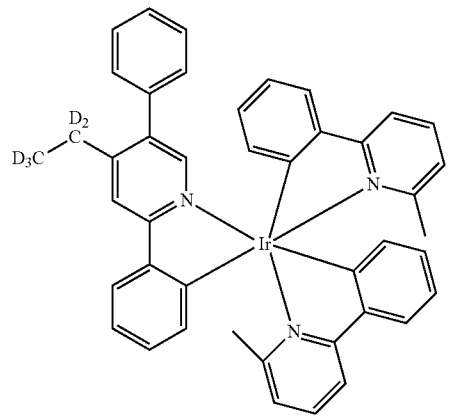
Compound 64
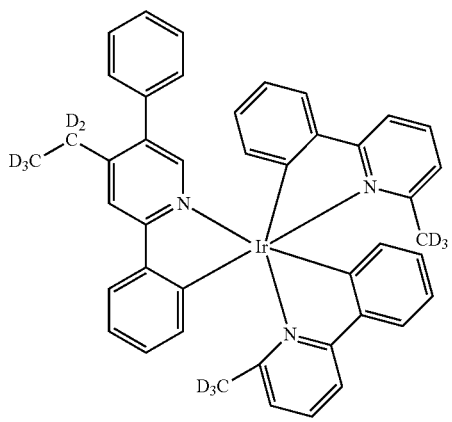

Compound 65
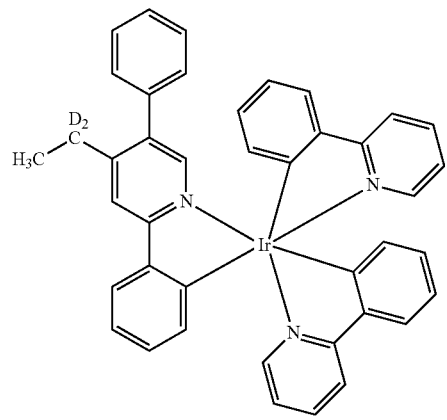
Compound 66
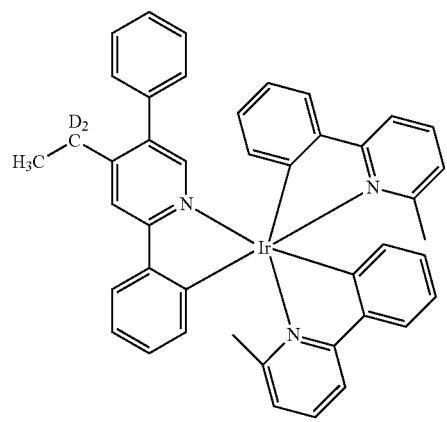
Compound 67
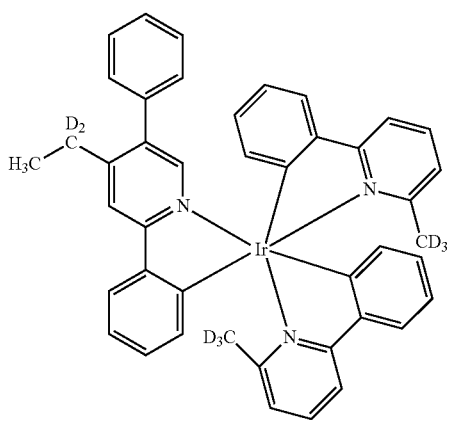
Compound 69
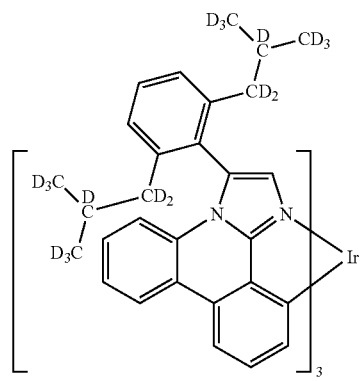
Compound 70
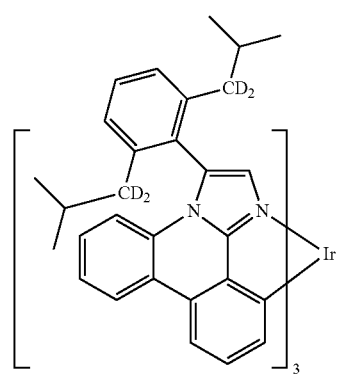
Compound 71
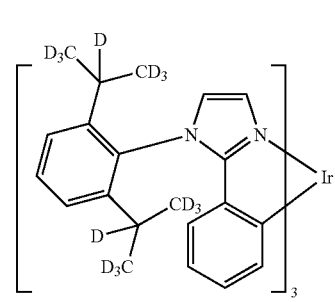
Compound 72
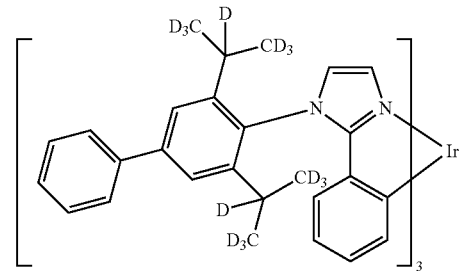
Compound 73
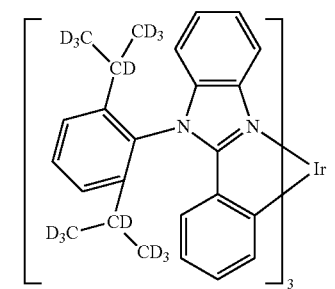

Compound 74
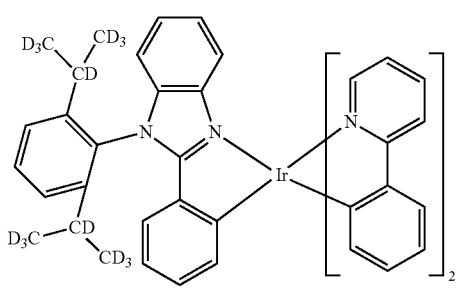
Compound 75
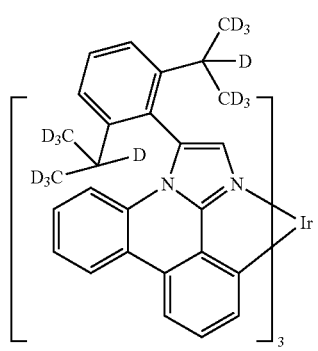
Compound 76
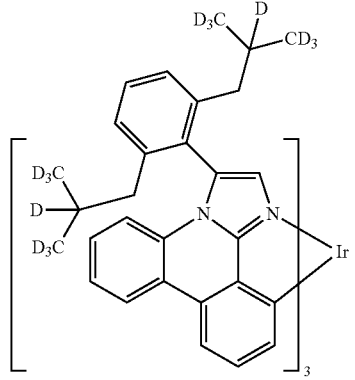
Compound 77
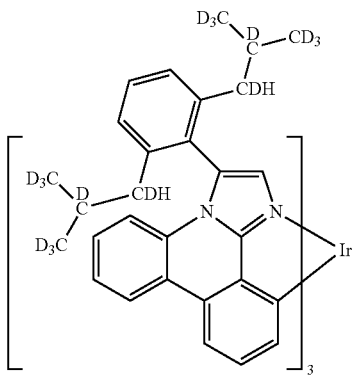
Compound 78
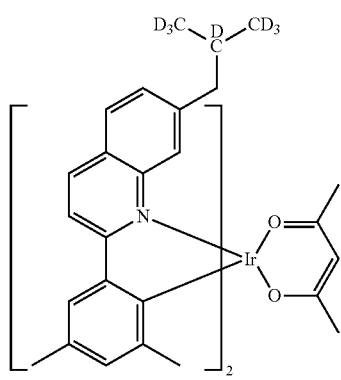
Compound 79
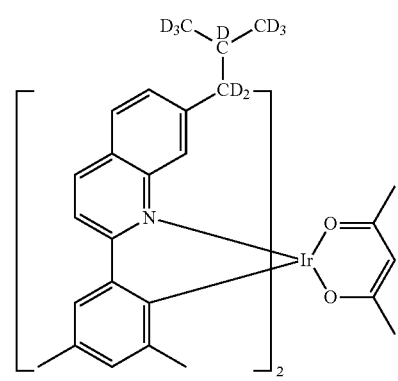
Compound 80
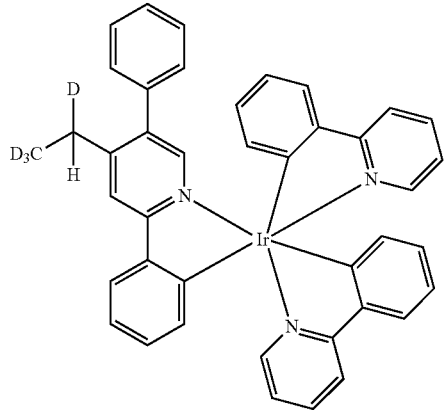
Compound 81
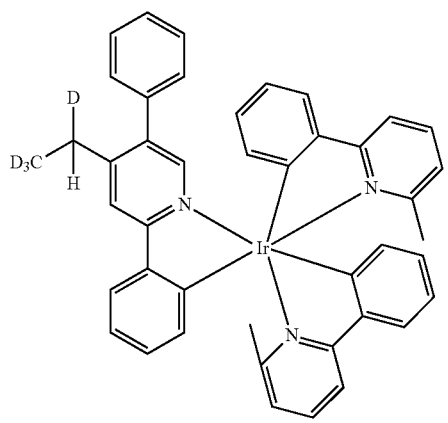

-continued

Compound 82

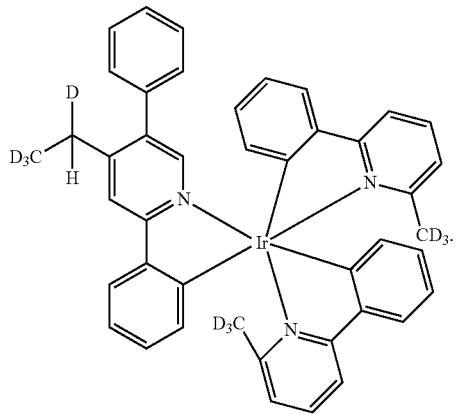

In one aspect, compounds are provided wherein the compound comprises a ligand having Formula II, for example, Compounds 2-4.

In another aspect, compounds are provided wherein the compound comprises a ligand having Formula III, for example, Compounds 5-9.

In another aspect, additional compounds comprising a ligand having Formula III are provided, including Compounds 58, 59, 69-70, and 75-77.

In yet another aspect, Compounds are provided wherein the compound comprises a ligand having Formula IV, for example, Compounds 10-14 and 27-40.

In another aspect, additional compounds comprising a ligand having Formula IV are provided, including Compounds 43-52, 62-67 and 80-82.

In yet another aspect, Compounds are provided wherein the compound comprises a ligand having Formula V, for example, Compounds 15-19.

In another aspect, additional compounds comprising a ligand having Formula V are provided, including Compounds 55-57, 73, and 74.

In yet another aspect, Compounds are provided wherein the compound comprises a ligand having Formula VI, for example, Compounds 20-23.

In another aspect, additional compounds comprising a ligand having Formula VI are provided, including Compounds 60, 61, 78 and 79.

In yet another aspect, Compounds are provided wherein the compound comprises a ligand having Formula VII, for example, Compounds 24-26, 41, and 42.

In a further aspect, compounds comprising a ligand having Formula III are provided, including Compounds 53, 54, 71 and 72.

The compounds comprising ligands having a formula selected from Formula II, Formula III, Formula IV, Formula V, Formula VI, and Formula VII may be particularly stable dopant compounds.

Additionally, compounds comprising ligands having Formula VIII may also be particularly stable compounds.

In one aspect, homoleptic compounds containing $CD_3$ are provided. In particular, compounds are provided wherein the ligand having FORMULA I is a ligand in a homoleptic compound. Homoleptic compounds provided herein include, for example, Compounds 2-19. In another aspect, heteroleptic compounds containing $CD_3$ are provided. In particular, compounds are provided wherein the ligand having FORMULA I is a ligand in a heteroleptic compound.

Heteroleptic compounds provided herein include, for example, Compounds 20-42. Heteroleptic compounds containing $CD_3$ may include compounds having an emissive ligand and a non-emissive ligand, such as Compounds 20-26 which contain two emissive ligands and an acac ligand. In addition, heteroleptic compounds containing $CD_3$ may include compounds wherein all of the ligands are emissive ligand and the emissive ligands have different structures. In one aspect, heteroleptic compounds containing $CD_3$ may have 2 emissive ligands including $CD_3$ and one emissive ligand that does not contain $CD_3$. For example, Compounds 27, 33, 35-40. In another aspect, heteroleptic compounds containing $CD_3$ may have 1 emissive ligand including $CD_3$ and 2 emissive ligands that do not contain $CD_3$. For example, Compounds 29-32, 41, and 42. The emissive ligand including $CD_3$ may include a single $CD_3$ group (e.g., Compounds 29-32) or the ligand may include several $CD_3$ groups (e.g., Compounds 41 and 42 contain one emissive ligand with 2 $CD_3$ substituents). In yet another aspect, heteroleptic compounds containing $CD_3$ may contain 2 or more different types of emissive ligands wherein all ligands contain $CD_3$. For example, Compounds 28 and 34.

Additionally, an organic light emitting device is provided. The device comprises include an anode, a cathode, and an organic emissive layer disposed between the anode and the cathode. The organic layer comprises a compound containing ligand having the structure:

FORMULA I

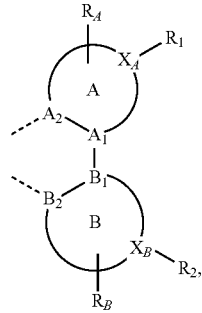

as described above. Selections for the aromatic rings, metal, and substituents described as preferred for compounds comprising a ligand having FORMULA I are also preferred for use in a device that includes a compound comprising a ligand having FORMULA I. These selections include those for metal M, rings A and B, and substituents $R_A$, $R_B$, $A_1$, $A_2$, $B_1$, $B_2$, $R_1$ and $R_2$.

A and B may independently represent a 5-membered or 6-membered aromatic or heteroaromatic ring. Preferably, A is selected from the group consisting of imidazole, pyrazole, triazole, oxazole, oxadiazole, pyridine, pyridazine, pyrimidine, pyrazine, and triazine. Preferably, B is selected from the group consisting of benzene, pyridine, furan, pyrrole, and thiophene. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked. $R_A$, $R_B$, $R_1$ and $R_2$ may be fused. The ligand is coordinated to a metal having an atomic weight greater than 40. Preferably, the metal is Ir.

In one aspect, the ligand has the structure:

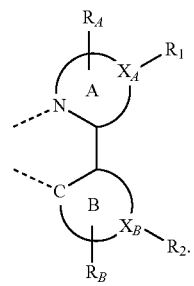

FORMULA Ia

In one aspect, $X_A$ and $X_B$ are independently C or N and when $X_A$ is N, $R_1$ is aryl. In another aspect, $X_A$ and $X_B$ are independently C or N and when $X_A$ is N, $R_1$ is phenyl further substituted with a group consisting of alkyl, alkoxy, amino, alkenyl, alkynyl, arylkyl, aryl, and heteroaryl and wherein the group includes at least one of CD, $CD_2$ or $CD_3$.

In one aspect, compounds are provided wherein at least 1 of the substituents of $R_A$ and $R_B$ is $CD_3$ attached directly to ring A, ring B, or a ring that is conjugated or fused to ring A or ring B.

As discussed above, the substituents $R_A$ and $R_B$ may be fused to ring A and/or ring B. The substituents $R_A$ and $R_B$ may be any substituents, including substituents that are linked, fused to ring A and/or ring B or not fused to ring A and/or ring B.

In particular, the organic layer of the device comprises a compound having a ligand selected from the group consisting of Formula II-VII. $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ is $CD_3$. Preferably, the organic layer comprises a compound selected from the group consisting of Compounds 2-42.

Additionally, the organic layer of the device comprises a compound having a ligand selected from the group consisting of Formula II-VII. $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylkyl, aryl, and heteroaryl. At least one of $R_1$, $R_2$, $R_3$, $R_4$, $R_5$, $R_6$, $R_7$, $R_8$, $R_9$, and $R_{10}$ includes $CD_3$.

Moreover, the organic layer of the device may comprise a compound having a ligand selected from the group consisting of Formula III-VIII. $R_1$, $R_2$, $R_3$, $R_4$, $R_5$, $R_6$, $R_7$, $R_8$, $R_9$, $R_{10}$, and $R_{11}$ are independently selected from the group consisting of hydrogen, alkyl, alkoxy, amino, alkenyl, alkynyl, arylkyl, aryl, and heteroaryl. $R_1$, $R_2$, $R_3$, $R_4$, $R_5$, $R_6$, $R_7$, $R_8$, $R_9$, $R_{10}$, and $R_{11}$ may be linked. $R_1$, $R_2$, $R_3$, $R_4$, $R_5$, $R_6$, $R_7$, $R_8$, $R_9$, $R_{10}$, and $R_{11}$ may be fused. At least one of $R_1$, $R_2$, $R_3$, $R_4$, $R_5$, $R_6$, $R_7$, $R_8$, $R_9$, $R_{10}$, and $R_{11}$ includes an alkyl group that includes CD, $CD_2$, or $CD_3$. Preferably, the organic layer comprises a compound selected from the group consisting of Compounds 43-82.

In one aspect, the organic layer is an emissive layer containing a compound provided having a ligand of FORMULA I, wherein the compound is an emitting dopant. The organic layer may further comprise a host. Preferably, the host has the formula:

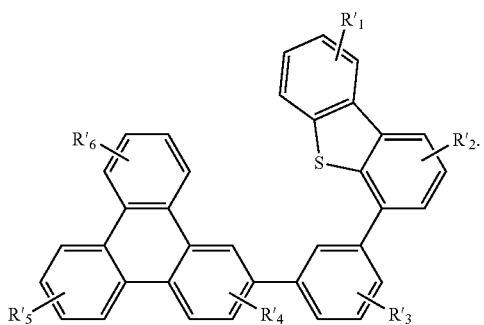

$R'_1$, $R'_2$, $R'_3$, $R'_4$, $R'_5$, and $R'_6$ may represent mono, di, tri, or tetra substitutions; and each of $R'_1$, $R'_2$, $R'_3$, $R'_4$, $R'_5$, and $R'_6$ are independently selected from the group consisting of hydrogen, alkyl and aryl. More preferably, the host is H1.

A consumer product comprising a device is also provided. The device comprises an anode, a cathode, and an organic layer disposed between the anode and the cathode. The organic layer comprises a compound containing a ligand having the structure:

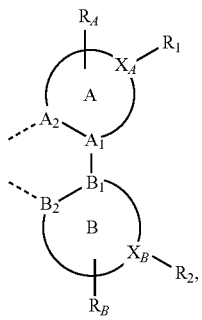

FORMULA I as described above. Selections for the aromatic rings, metal, and substituents described as preferred for compounds comprising a ligand having FORMULA I are also preferred for use in a device that includes a compound comprising a ligand having FORMULA I. These selections include those for metal M, rings A and B, and substituents $R_A$, $R_B$, $A_1$, $A_2$, $B_1$, $B_2$, $R_1$ and $R_2$.

A and B may independently represent a 5-membered or 6-membered aromatic or heteroaromatic ring. Preferably, A is selected from the group consisting of imidazole, pyrazole, triazole, oxazole, oxadiazole, pyridine, pyridazine, pyrimidine, pyrazine, and triazine. Preferably, B is selected from the group consisting of benzene, pyridine, furan, pyrrole, and thiophene. $A_1$, $A_2$, $B_1$, and $B_2$ are independently C or N. $R_A$ and $R_B$ may represent mono, di, or tri substitutions. $X_A$ and $X_B$ are independently C or a heteroatom. $R_A$, $R_B$, $R_1$ and $R_2$ are independently selected from the group consisting of hydrogen, alkyl, alkoxy, amino, alkenyl, alkynyl, arylkyl, aryl, and heteroaryl. At least one of $R_A$, $R_B$, $R_1$ and $R_2$ includes CD, $CD_2$ or $CD_3$. Preferably, at least one of $R_A$, $R_B$, $R_1$ and $R_2$ includes $CD_3$. $R_A$, $R_B$, $R_1$ and $R_2$ may be linked. $R_A$, $R_B$, $R_1$ and $R_2$ may be fused. The ligand is coordinated to a metal having an atomic weight greater than 40. Preferably, the metal is Ir.

In one aspect, $X_A$ and $X_B$ are independently C or N and when $X_A$ is N, $R_1$ is aryl. In another aspect, $X_A$ and $X_B$ are independently C or N and when $X_A$ is N, $R_1$ is phenyl further substituted with a group consisting of alkyl, alkoxy, amino, alkenyl, alkynyl, arylkyl, aryl, and heteroaryl and wherein the group includes at least one of CD, $CD_2$ or $CD_3$.

The consumer product may comprise a device further comprising an organic layer containing a compound comprising a ligand having the structure selected from the group consisting of Formula II-VII. In particular, the compound may be selected from the group consisting of Compounds 2-42.

Moreover, the organic layer of the device may comprise a compound having a ligand selected from the group consisting of Formula III-VIII. Preferably, the organic layer comprises a compound selected from the group consisting of Compounds 43-82.

In one aspect, particular consumer products comprising a device are provided. Preferably, the device contains compounds wherein at least 1 of the substituents of $R_A$ and $R_B$ is $CD_3$ attached directly to ring A, ring B, or a ring that is conjugated or fused to ring A or ring B.

As discussed above, the substituents $R_A$ and $R_B$ may be fused to ring A and/or ring B. The substituents $R_A$ and $R_B$ may be any substituents, including substituents that are linked, fused to ring A and/or ring B or not fused to ring A and/or ring B.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphryin compounds | 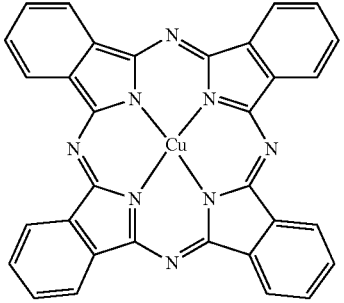 | Appl. Phys. Lett. 69, 2160 (1996) |
| Starburst triarylamines | 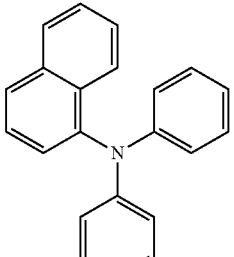 | J. Lumin. 72-74, 985 (1997) |
| $CF_x$ Fluorohydrocarbon polymer | 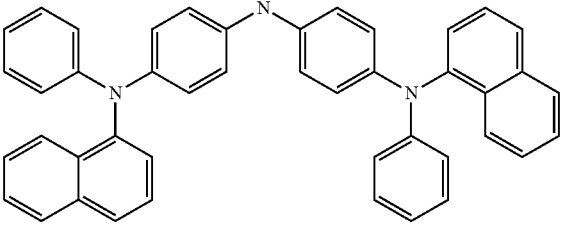 | Appl. Phys. Lett. 78, 673 (2001) |

TABLE 1-continued

| MATERIAL | EXAMPLES OF MATERIAL | PUBLICATIONS |
| --- | --- | --- |
| Conducting polymers (e.g., PEDOT: PSS, polyaniline, polypthiophene) | | Synth. Met. 87, 171 (1997) |
| Arylamines complexed with metal oxides such as molybdenum and tungsten oxides | | SID Symposium Digest, 37, 923 (2006) |
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

TABLE 1-continued
| MATERIAL | EXAMPLES OF MATERIAL | PUBLICATIONS |
|---|---|---|
|  | 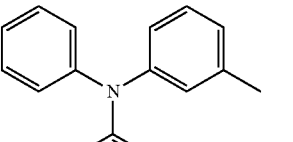 | J. Mater. Chem. 3, 319 (1993) |
|  | 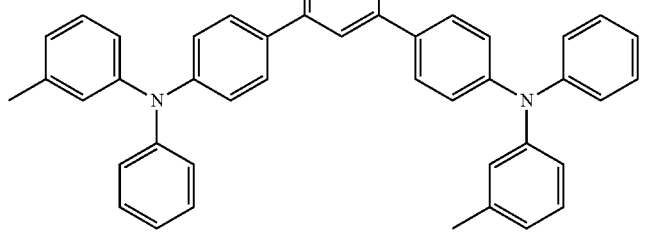 | Appl. Phys. Lett. 90, 183503 (2007) |
|  | 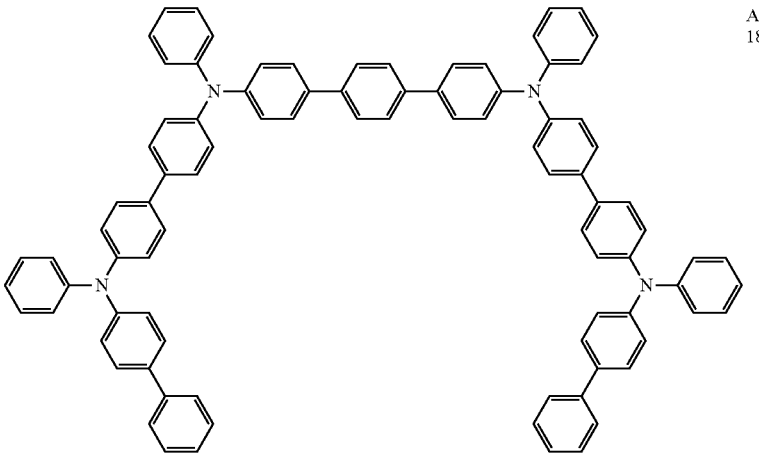 | Appl. Phys. Lett. 90, 183503 (2007) |
| Triaylamine on spirofluorene core | 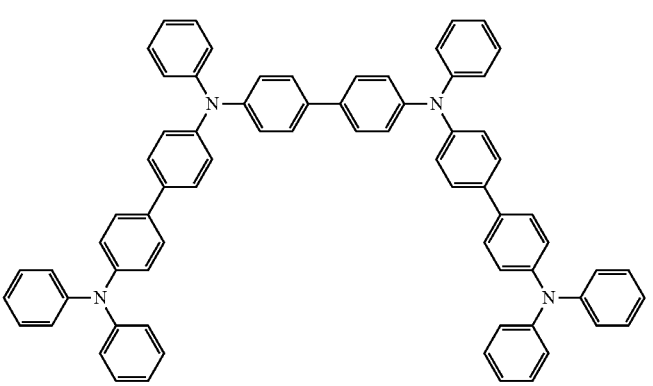 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Synth. Met. 91, 209 (1997) |

TABLE 1-continued
| MATERIAL | EXAMPLES OF MATERIAL | PUBLICATIONS |
|---|---|---|
| Arylamine carbazole compounds | 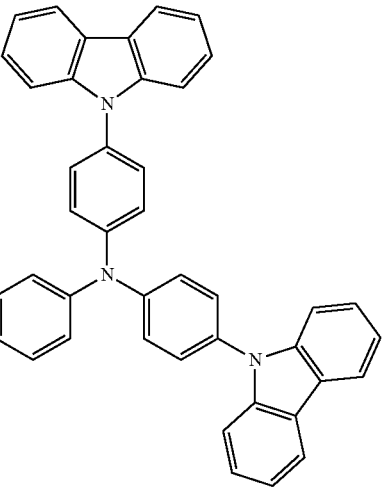 | Adv. Mater. 6, 677 (1994) |
| Indolocarbazoles | 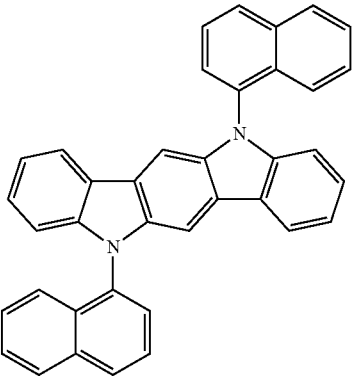 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 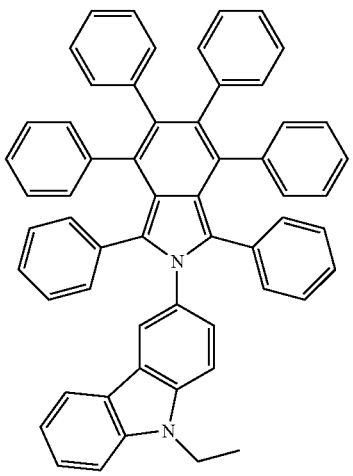 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 1-continued

| MATERIAL | EXAMPLES OF MATERIAL | PUBLICATIONS |
|---|---|---|
| | Phosphorescent OLED host materials | |
| | Red hosts | |
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 1-continued
| MATERIAL | EXAMPLES OF MATERIAL | PUBLICATIONS |
|---|---|---|
| | Green hosts | |
| Arylcarbazoles | 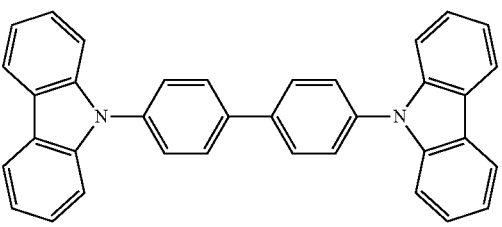 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 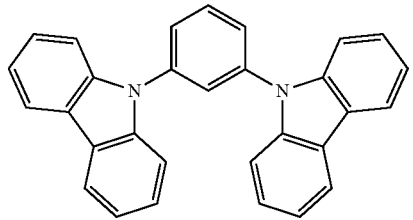 [SMILES: c1cc(-n2c3ccccc3c3ccccc32)cc(-n2c3ccccc3c3ccccc32)c1] | US2003175553 |
| | 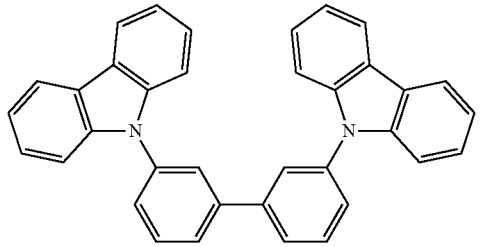 [SMILES: c1cc(-c2cccc(-n3c4ccccc4c4ccccc43)c2)cc(-n2c3ccccc3c3ccccc32)c1] | WO2001039234 |
| Aryltriphenylene compounds | 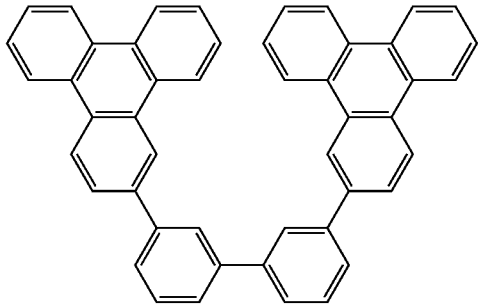 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 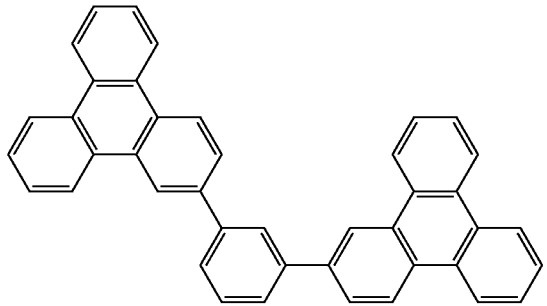 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 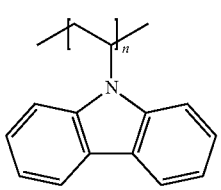 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 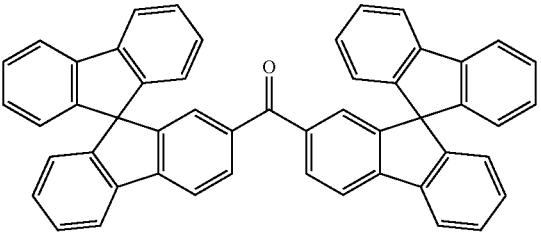 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 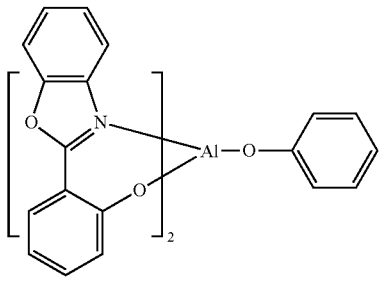 | WO05089025 |
| | 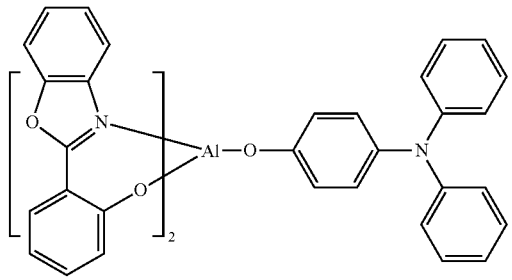 | WO06132173 |
| | 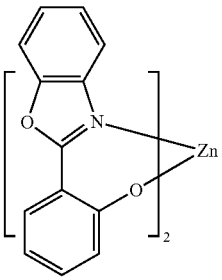 | JP200511610 |
| Spirofluorene-carbazole compounds | 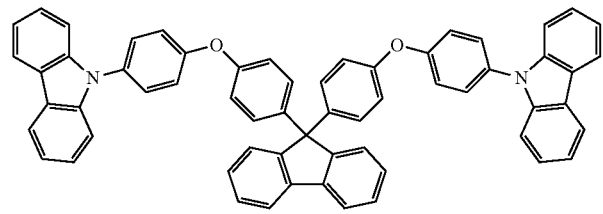 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 1-continued
| MATERIAL | EXAMPLES OF MATERIAL | PUBLICATIONS |
|---|---|---|
| | 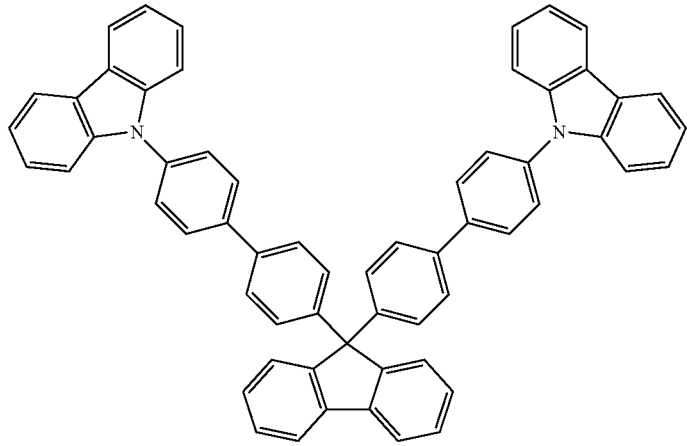 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 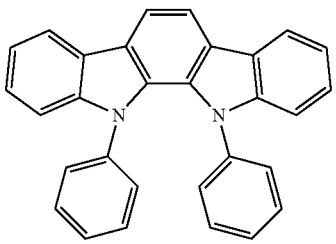 [SMILES: c1ccc(-n2c3ccccc3c3ccc4c5ccccc5n(-c5ccccc5)c4c32)cc1] | WO07063796 |
| | 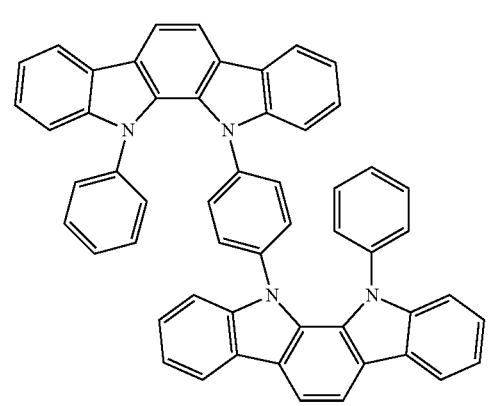 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO07063754 |
| 5-member ring electron deficient heterocycles (e.g., triazole, oxadiazole) | 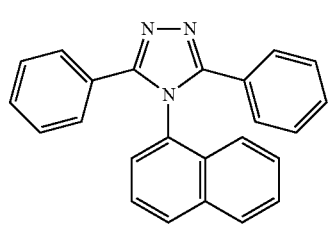 [SMILES: c1ccc(-c2nnc(-c3ccccc3)n2-c2cccc3ccccc23)cc1] | J. Appl. Phys. 90, 5048 (2001) |
| | 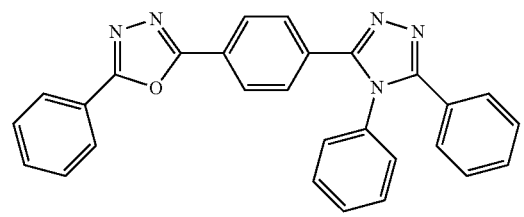 [SMILES: c1ccc(-c2nnc(-c3ccc(-c4nnc(-c5ccccc5)n4-c4ccccc4)cc3)o2)cc1] | WO04107822 |

TABLE 1-continued
| MATERIAL | EXAMPLES OF MATERIAL | PUBLICATIONS |
|---|---|---|
| Metal phenoxypyridine compounds | 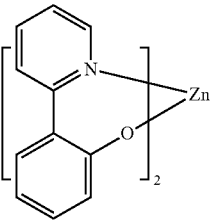 | WO05030900 |
Blue hosts
| | | |
|---|---|---|
| Arylcarbazoles | 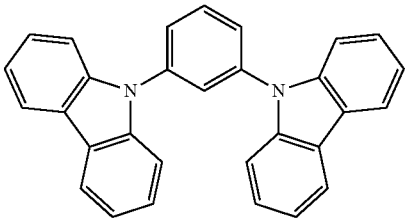 [SMILES: c1cc(-n2c3ccccc3c3ccccc32)cc(-n2c3ccccc3c3ccccc32)c1] | Appl. Phys. Lett, 82, 2422 (2003) |
| | 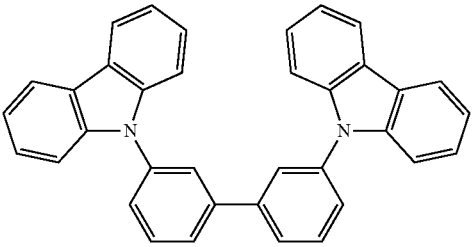 [SMILES: c1cc(-c2cccc(-n3c4ccccc4c4ccccc43)c2)cc(-n2c3ccccc3c3ccccc32)c1] | US20070190359 |
| Dibenzothiophene-carbazole compounds | 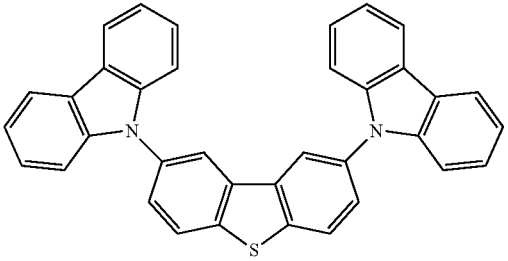 [SMILES: c1ccc2c(c1)c1ccccc1n2-c1ccc2sc3ccc(-n4c5ccccc5c5ccccc54)cc3c2c1] | WO2006114966 |
Phosphorescent dopants
Red dopants
| | | |
|---|---|---|
| Heavy metal porphyrins (e.g., PtOEP) | 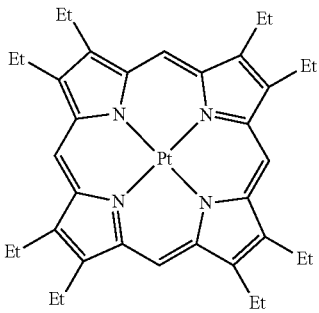 | Nature 395, 151 (1998) |

TABLE 1-continued

| MATERIAL | EXAMPLES OF MATERIAL | PUBLICATIONS |
| --- | --- | --- |
| Iridium(III) organometallic complexes | | Appl. Phys. Lett. 78, 1622 (2001) |
| | | US06835469 |
| | | US06835469 |
| | | US20060202194 |
| | | US20060202194 |

TABLE 1-continued

| MATERIAL | EXAMPLES OF MATERIAL | PUBLICATIONS |
|---|---|---|
|  |  | US07087321 |
|  |  | US07087321 |
|  |  | Adv. Mater. 19, 739 (2007) |
| Platinum(II) organometallic complexes |  | WO2003040257 |
| Osminum(III) complexes |  | Chem. Mater. 17, 3532 (2005) |
| Ruthenium(II) complexes |  | Adv. Mater. 17, 1059 (2005) |

TABLE 1-continued
| MATERIAL | EXAMPLES OF MATERIAL | PUBLICATIONS |
| --- | --- | --- |
| | Green dopants | |
| Iridium(III) organometallic complexes | and its derivatives | Inorg. Chem. 40, 1704 (2001) |
| | | US2002034656 |
| | | US06687266 |
| | | Chem. Mater. 16, 2480 (2004) |
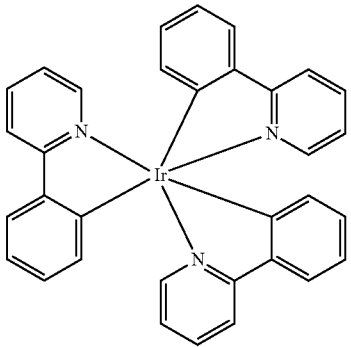

TABLE 1-continued

| MATERIAL | EXAMPLES OF MATERIAL | PUBLICATIONS |
|---|---|---|
| | | US2007190359 |
| | | US 2006008670<br>JP2007123392 |
| | | Adv. Mater. 16, 2003 (2004) |
| | | Angew. Chem. Int. Ed. 2006, 45, 7800 |
| Pt(II) organometallic complexes | | Appl. Phys. Lett. 86, 153505 (2005) |

TABLE 1-continued
| MATERIAL | EXAMPLES OF MATERIAL | PUBLICATIONS |
|---|---|---|
| | 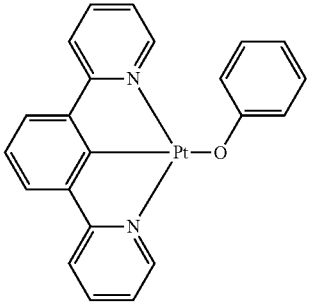 | Appl. Phys. Lett. 86, 153505 (2005) |
| | 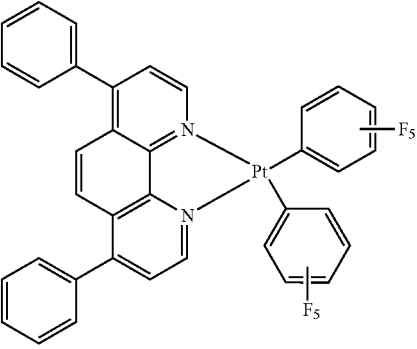 | Chem. Lett. 34, 592 (2005) |
| Gold complexes | 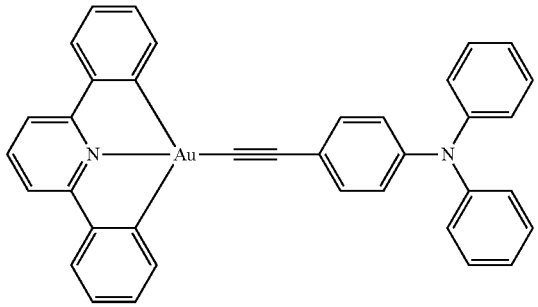 | Chem. Commun. 2906 (2005) |
| Rhenium(III) complexes | 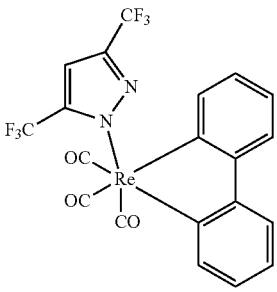 | Inorg. Chem. 42, 1248 (2003) |
| Blue dopants | | |
| Iridium(III) organometallic complexes | 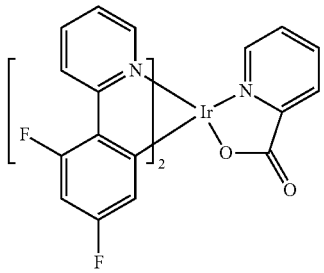 | WO2002002714 |

TABLE 1-continued
| MATERIAL | EXAMPLES OF MATERIAL | PUBLICATIONS |
|---|---|---|
| | 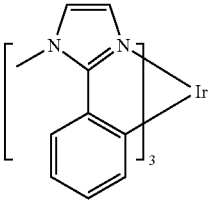 | WO2006009024 |
| | 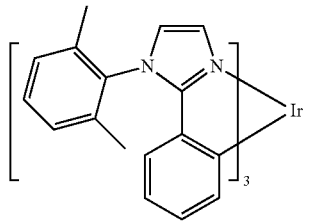 | US2006251923 |
| | 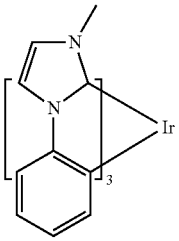 | WO2006056418, US2005260441 |
| | 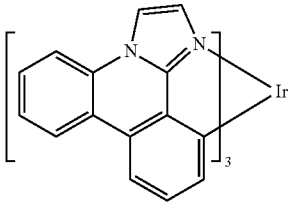 | US2007190359 |
| | 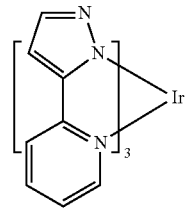 | US2002134984 |
| | 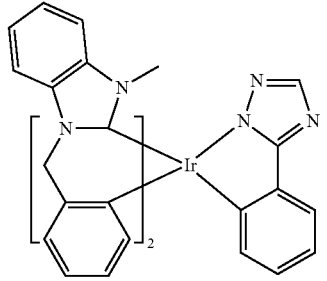 | Angew. Chem. Int. Ed. 47, 1 (2008) |

TABLE 1-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO05123873 |
| | | WO05123873 |
| | | WO07004380 |

TABLE 1-continued
| MATERIAL | EXAMPLES OF MATERIAL | PUBLICATIONS |
|---|---|---|
| | 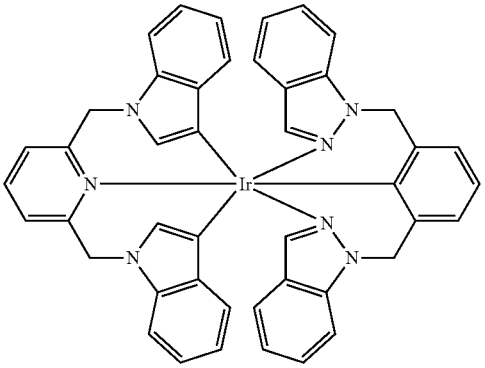 | WO06082742 |
| Osmium(II) complexes | 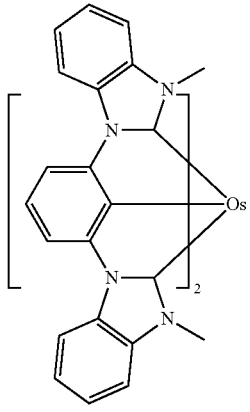 | US2005260449 |
| | 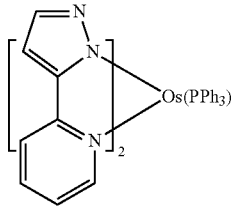 | Organometallics 23, 3745 (2004) |
| Gold complexes | 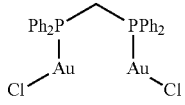 | Appl. Phys. Lett. 74, 1361 (1999) |
| Platinum(II) complexes | 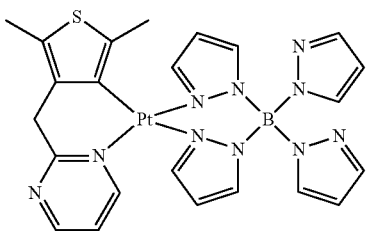 | WO06098120, WO06103874 |

TABLE 1-continued
| MATERIAL | EXAMPLES OF MATERIAL | PUBLICATIONS |
|---|---|---|
| | Exciton/hole blocking layer materials | |
| Bathocuprine compounds (e.g., BCP, BPhen) | 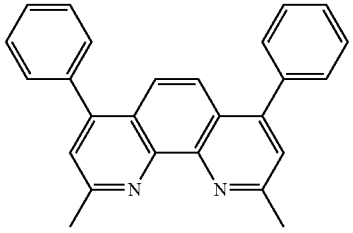 [SMILES: Cc1cc(-c2ccccc2)c2ccc3c(-c4ccccc4)cc(C)nc3c2n1] | Appl. Phys. Lett. 75, 4 (1999) |
| | 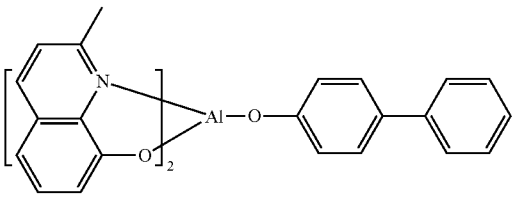 | Appl. Phys. Lett. 79, 449 (2001) |
| Metal 8-hydroxyquinolates (e.g., BAlq) | 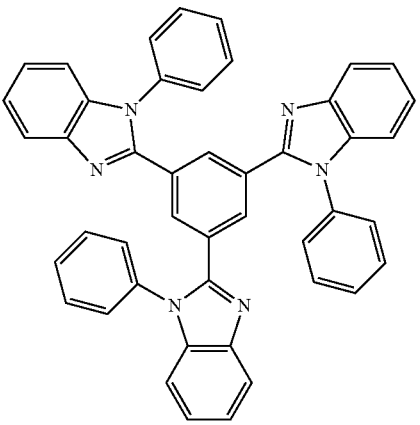 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 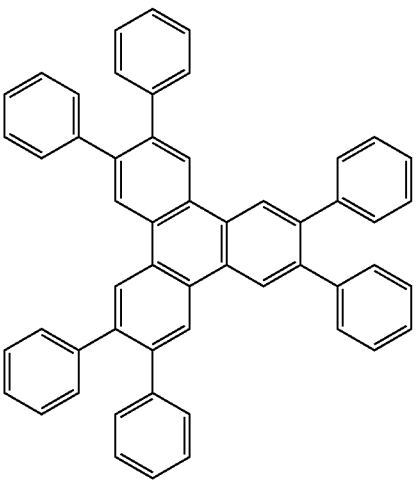 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 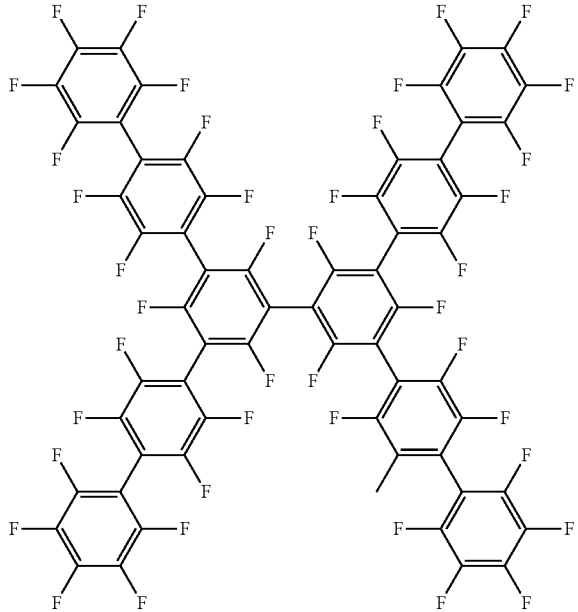 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 1-continued

| MATERIAL | EXAMPLES OF MATERIAL | PUBLICATIONS |
| --- | --- | --- |
| Electron transporting materials | | |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., $Alq_3$) | | Appl. Phys. Lett. 51, 913 (1987) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued

| MATERIAL | EXAMPLES OF MATERIAL | PUBLICATIONS |
| --- | --- | --- |
| 5-member ring electron deficient heterocycles (e.g.,triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |

EXPERIMENTAL

Compound Examples

Example 1

Synthesis of Compound 10

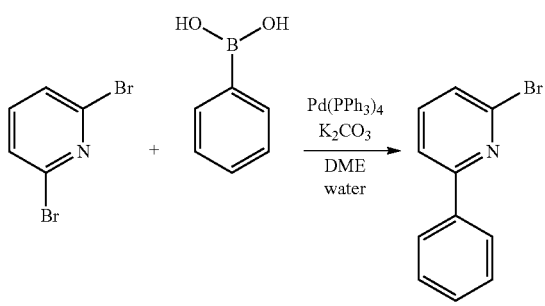 [SMILES: Brc1cccc(Br)n1 ; OB(O)c1ccccc1 ; Brc1cccc(-c2ccccc2)n1]

Synthesis of 2-bromo-6-phenylpyridine. In a 3-neck 1 L round-bottom flask fitted with a condenser, nitrogen inlet, and 2 stoppers was added 2,6-dibromopyridine (15.3 g, 64.58 mmol), phenylboronic acid (7.87 g, 64.58 mmol), and potassium carbonate (17.85 g, 129.16 mmol) in 228 mL of dimethoxyethane and 150 mL of water. Nitrogen was bubbled directly into the mixture for 15 minutes. Tetrakis (triphenylphosphine)palladium (0) was added (1.85 g, 1.60 mmol) and the reaction mixture was heated to reflux. The reaction was complete after 3 h of heating. It was cooled to room temperature and diluted with water and ethyl acetate. The layers were separated and the aqueous layer extracted with ethyl acetate. The organic layers were dried over magnesium sulfate, filtered, and evaporated. The material was purified by column chromatography eluting with 2% ethyl acetate/hexanes followed by vacuum distillation using a Kugelrohr collecting product at 150° C. 5.2 g of product was obtained (34%)

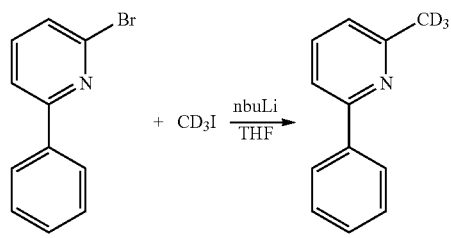

Synthesis of 2-phenyl-6-methyl-d3-phenylpyridine. A 3-neck 500 mL round-bottom flask equipped with a dropping funnel, nitrogen inlet, and a stopper was dried by heating with a heat gun under vacuum. To the cooled, dry flask was added 2-bromo-6-phenylpyridine (11.3 g, 48.27 mmol) and 100 mL of dry THF. The solution was cooled in a dry ice/acetone bath under nitrogen and iodomethane-$d_3$ was added dropwise (6 mL, 96.54 mmol). The solution was stirred cold 1 h then allowed to warm to room temperature overnight. It was diluted with water and extracted twice with ethyl acetate. The organic layers were dried over magnesium sulfate, filtered and evaporated. The crude material was purified by column chromatography twice eluting with 2% ethyl acetate/hexanes. 5.8 g of 2-phenyl-6-methyl-d3-pyridine was obtained (70%).

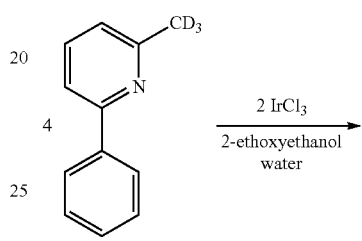

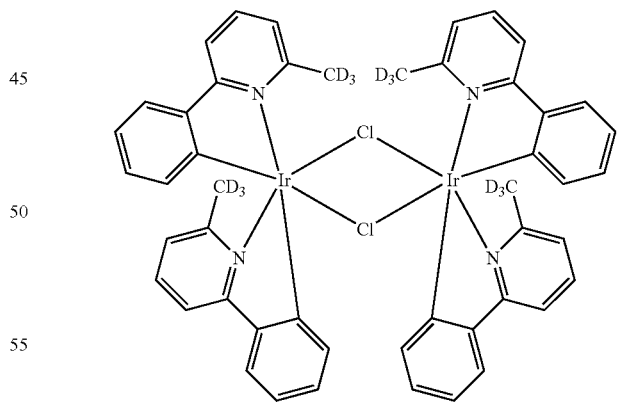

Synthesis of Dimer. A mixture of 2-phenyl-6-methyl($d_3$) pyridine (1.65 g, 9.58 mmol), iridium chloride (1.6 g, 4.35 mmol), and 30 mL of 2-ethoxyethanol were heated to reflux overnight under nitrogen. The mixture was cooled to room temperature and a red solid was filtered off. The solid was washed with methanol and hexanes and air dried in a fume hood. 1.09 g of product was obtained (44%) of dimer which was used as is in the next step.

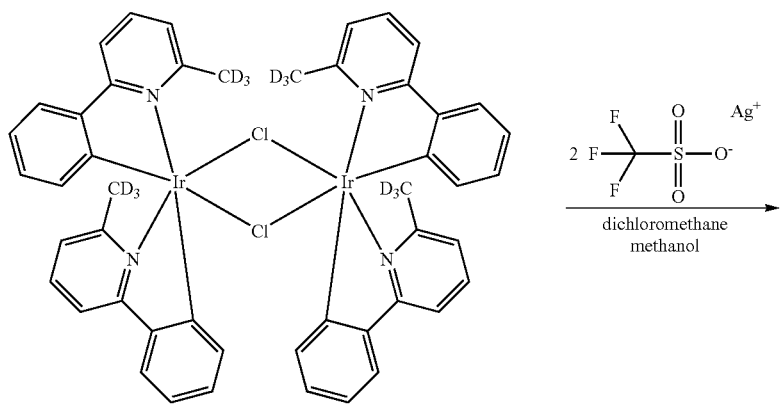

Synthesis of triflate intermediate. A mixture was prepared of dimer (1.09 g, 0.956 mmol) and 125 mL dichloromethane in a 250 mL round-bottom flask. Silver triflate (0.51 g, 2.00 mmol) in 10 mL of methanol was added to the red mixture and it turned green. The contents of the flask were stirred overnight under nitrogen at room temperature. The mixture was filtered through a pad of Celite and the Celite rinsed with dichloromethane. The filtrate was evaporated to yield a greenish-yellow solid. The solid was dried under high vacuum. 1 g of solid was obtained (71%) and used as is in the next reaction.

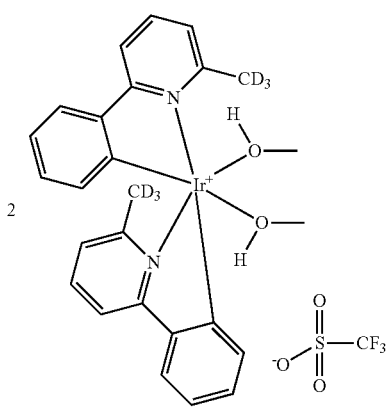

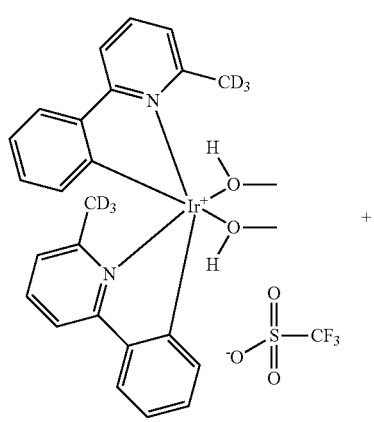

-continued

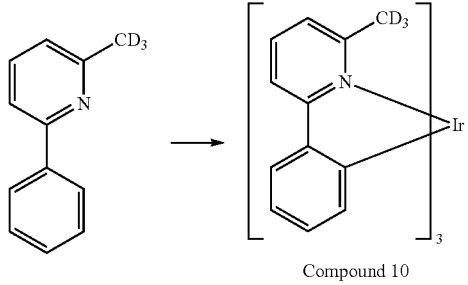

Compound 10

Synthesis of Compound 10. In a 50 mL glass tube was added the triflate complex (1 g, 1.3 mmol) and 2-phenyl-6-methyl(d$_3$)pyridine (0.7 g, 4.0 mmol) and the tube was evacuated and replaced with nitrogen. This procedure was repeated and the tube subsequently heated to 200° C. under nitrogen overnight. The tube was cooled and dichloromethane was added to dissolve material to transfer to a flask. The crude material was purified by column chromatography eluting with 20, 40, and 50% dichloromethane/hexanes followed by sublimation at 250° C. 0.58 g of product was obtained (63%) after sublimation.

Example 2

Synthesis of Compound 13

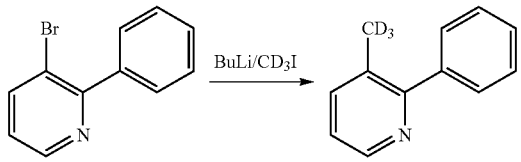 [SMILES: Brc1cccnc1-c1ccccc1 ; [2H]C([2H])([2H])c1cccnc1-c1ccccc1]

Synthesis of 3-methyl-d3-2-phenylpyridine. 3-bromo-2-phenylpyridine (9.9 g, 42 mmol) was dissolved in 100 mL of tetrahydrofuran and cooled to −78° C. To the solution was added BuLi (26.4 mL, 1.6 M in hexanes) dropwise. The reaction mixture was stirred at −78° C. for 1 h after the addition was complete. Methyl-$d_3$ iodide (9.3 g, 63 mmol) was added and warmed to room temperature for 2 h. The reaction was then quenched with water and extracted with ethyl acetate. The crude product was purified by column using hexanes and ethyl acetate as eluent. 2.3 g of pure product was obtained after purification.

Compound 13

Synthesis of Compound 13. 3-methyl-d3-2-phenylpyridine (1.8 g, 10.4 mmol) and Ir(acac)$_3$ (0.64 g, 1.3 mmol) was heated up to 260° C. for 48 h under nitrogen. After cooled to room temperature, dichloromethane was added to dissolve the product. The dichloromethane solution was then poured into hexanes. The precipitate was collected and run through a silica gel plug. 0.6 g of product was obtained. The product was further purified by recrystallizing from 1,2-dichlorobenzene.

Example 3

Synthesis of Compound 27

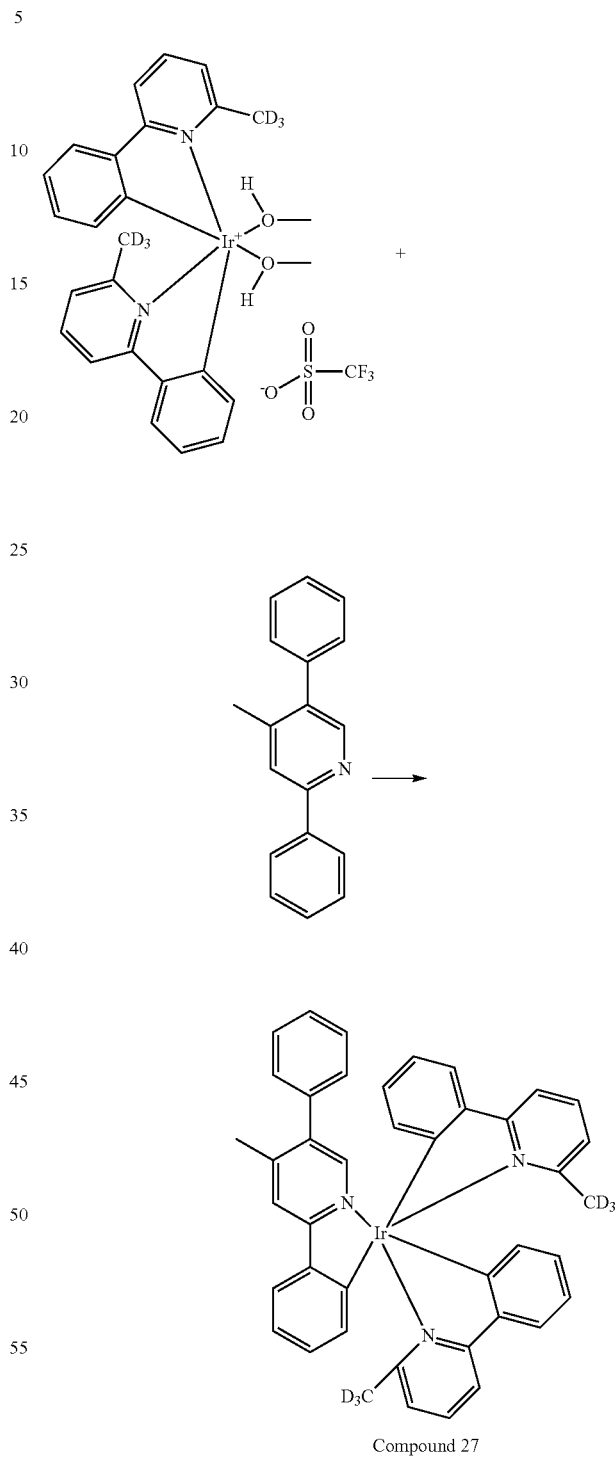

Compound 27

Synthesis of Compound 27. The triflate complex (1.4 g), 4-methyl-2,5-diphenylpyridine (1.5 g), and 50 mL of ethanol were mixed and heated up to reflux under nitrogen overnight. The precipitate was filtered. The crude material was purified by column chromatography eluting with 50% dichloromethane/hexanes. 1.1 g of desired product was obtained.

Example 4

Synthesis of Compound 43

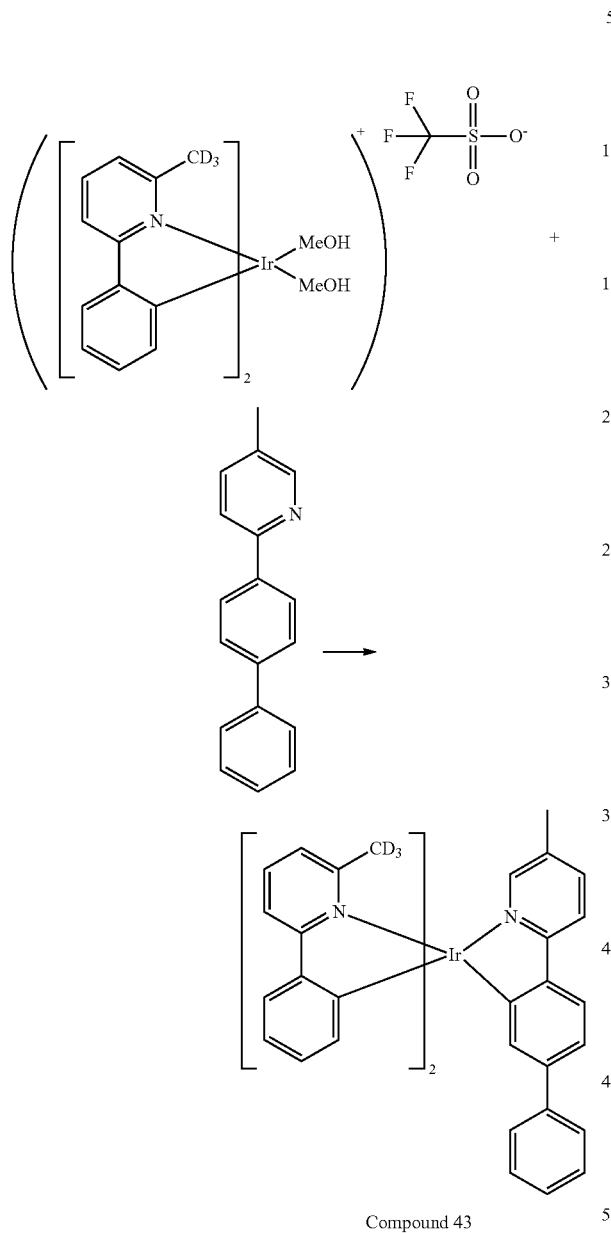

Compound 43

Synthesis of Compound 43. The Iridium triflate complex (1.0 g, 1.3 mmol) and 2-biphenyl-4-methylpyridine (1.0 g, 4 mmol) was place in a 100 mL round bottom flask. 20 mL of a 50:50 solution of ethanol and methanol was added to the flask. The reaction mixture was refluxed for 8 h. The reaction mixture was then allowed to cool to room temperature. The reaction mixture was poured onto a silica plug and was washed with ethanol followed by hexanes. The filtrate was discarded. The plug was then washed with dichloromethane to elute the product. The solvent from the filtrate was removed on the rotary evaporator. The product was further purified using column chromatography with 50:50 dichloromethane and hexanes as the eluent to yield 0.5 g (50% yield) of product.

Example 5

Synthesis of Compound 50

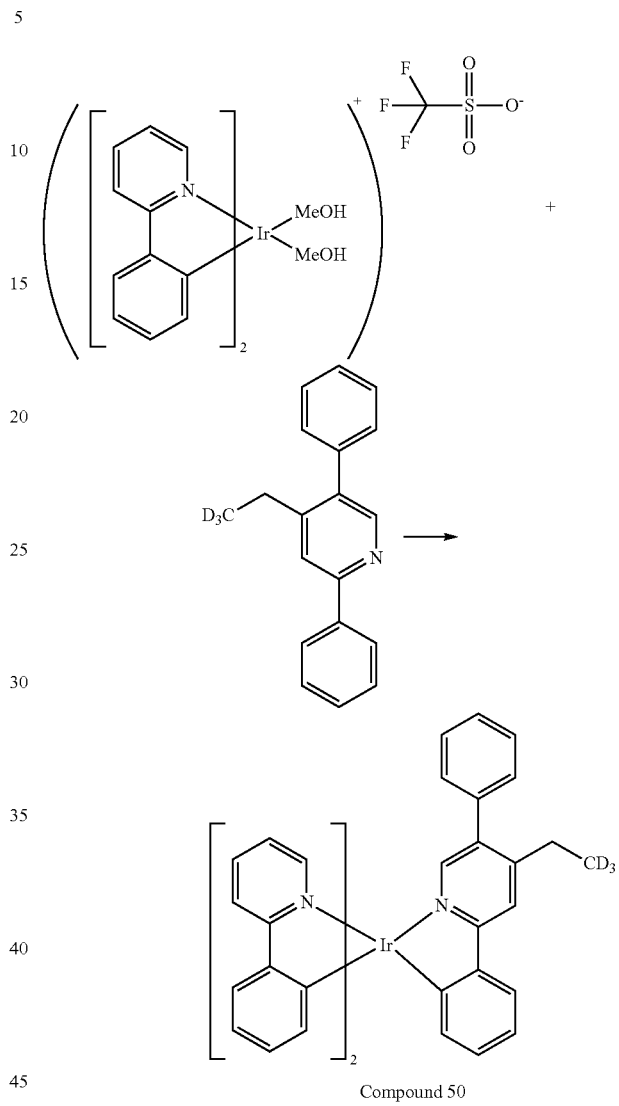

Compound 50

Synthesis of Compound 50. The Iridium triflate complex (6.58 g, 9.2 mmol) and 4-(ethyl,$d_3$)-2,5-diphenylpyridine (6.58 g, 25.0 mmol) was place in a 1000 mL round bottom flask. 140 mL of a 50:50 solution of ethanol and methanol was added to the flask. The reaction mixture was refluxed for 8 h. The reaction mixture was then allowed to cool to room temperature. The reaction mixture was poured onto a silica plug and was washed with ethanol followed by hexanes. The filtrate was discarded. The plug was then washed with dichloromethane to elute the product. The solvent from the filtrate was removed on the rotary evaporator. The product was further purified using column chromatography with 50:50 dichloromethane and hexanes as the eluent to yield 3.8 g (54% yield) of product.

Device Examples

All devices are fabricated by high vacuum (<$10^{-7}$ Torr) thermal evaporation. The anode electrode is 1200 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Particular devices are provided wherein inventive compounds, Compound 10, Compound 13, and Compound 27, are the emitting dopant and H1 is the host. All device examples have organic stacks consisting of sequentially, from the ITO surface, 100 Å of E1 as the hole injecting layer (HIL), 300 Å of 4,4'-bis[N-(1-naphthyl)-N-phenylamino] biphenyl (α-NPD) as the hole transport layer (HTL), 300 Å of H1, a host material, doped with 7% or 10% of the invention compound, as the emissive layer (EML), 50 Å of H1 as the blocking layer (BL) and 400 Å of $Alq_3$ (tris-8-hydroxyquinoline aluminum) as the ETL.

Comparative Examples 1-5 were fabricated similarly to the Device Examples, except the materials used in the EML and the BL differed. In particular, E1, E2, or E3 was used as the emitting dopant used in the EML of Comparative Examples 1 and 2, 3, 4 and 5, respectively. In addition, HPT was the BL material in Comparative Example 3.

As used herein, the following compounds have the following structures:

H1
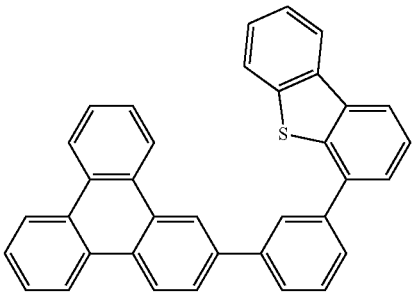

H2
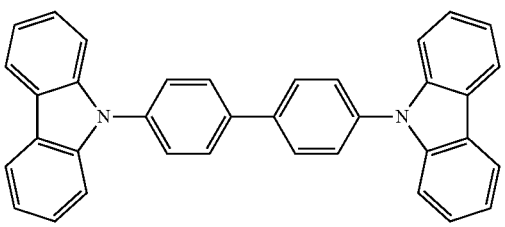

E1
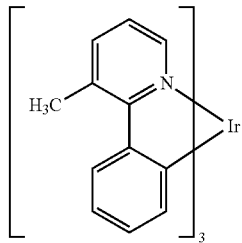

E2
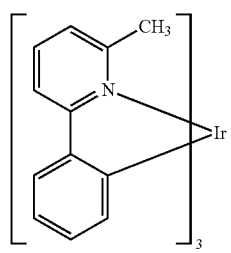

Compound 10
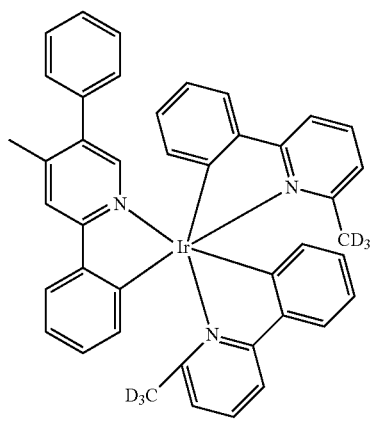

Compound 13

Compound 27

E3
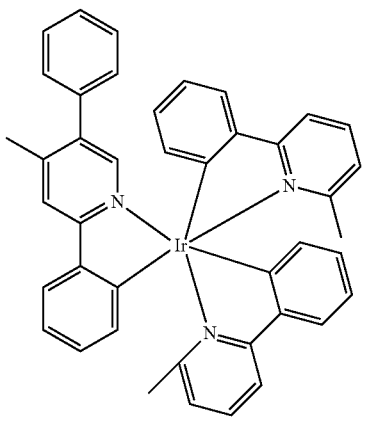

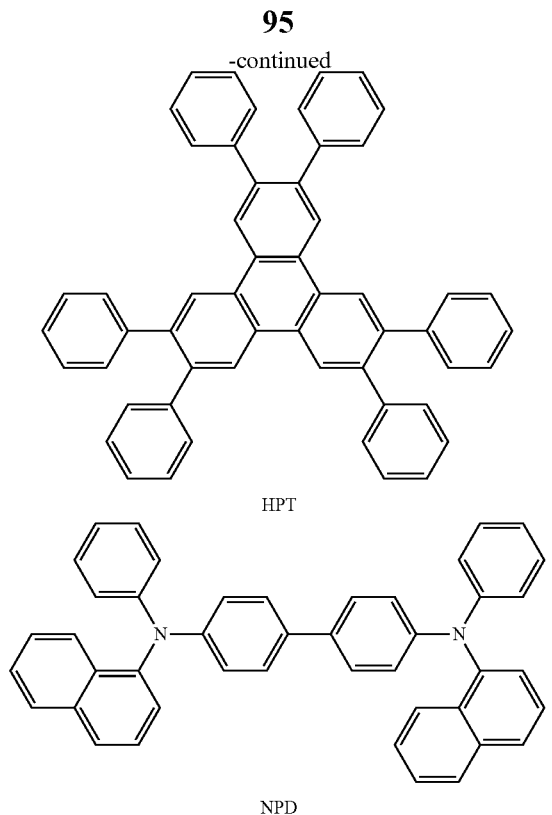

HPT

NPD

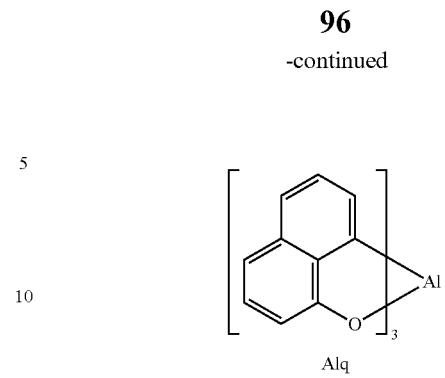

Alq

Particular materials for use in an OLED are provided. In particular, the materials may be used as emitting dopants in the emissive layer (EML) of such a device. The compounds provided herein may be used to improve color, efficiency, and lifetime in devices. Cmpd is an abbreviation of Compound. Ex. is an abbreviation of Example. Comp. is an abbreviation of Comparative.

TABLE 2

| Example | HIL | HTL | Host | A | % | BL | ETL |
|---|---|---|---|---|---|---|---|
| Ex. 1 | E1 100 Å | NPD 300 Å | H1 | Cmpd 10 | 7% | H1 50 Å | Alq 400 Å |
| Ex. 2 | E1 100 Å | NPD 300 Å | H1 | Cmpd 10 | 10% | H1 50 Å | Alq 400 Å |
| Ex. 3 | E1 100 Å | NPD 300 Å | H1 | Cmpd 13 | 7% | H1 50 Å | Alq 400 Å |
| Ex. 4 | E1 100 Å | NPD 300 Å | H1 | Cmpd 13 | 10% | H1 50 Å | Alq 400 Å |
| Ex. 5 | E1 100 Å | NPD 300 Å | H1 | Cmpd 27 | 7% | H1 50 Å | Alq 400 Å |
| Ex. 6 | E1 100 Å | NPD 300 Å | H1 | Cmpd 27 | 10% | H1 50 Å | Alq 400 Å |
| Comp. Ex. 1 | E1 100 Å | NPD 300 Å | H1 | E1 | 7% | H1 50 Å | Alq 400 Å |
| Comp. Ex. 2 | E1 100 Å | NPD 300 Å | H1 | E1 | 10% | H1 50 Å | Alq 400 Å |
| Comp. Ex. 3 | E1 100 Å | NPD 300 Å | H2 | E2 | 10% | HPT 50 Å | Alq 400 Å |
| Comp. Ex. 4 | E1 100 Å | NPD 300 Å | H1 | E3 | 7% | H1 50 Å | Alq 400 Å |
| Comp. Ex. 5 | E1 100 Å | NPD 300 Å | H1 | E3 | 10% | H1 50 Å | Alq 400 Å |

TABLE 3

| | | | | | At 1000 nits | | | | At 40 mA/cm$^2$ | |
|---|---|---|---|---|---|---|---|---|---|---|
| | $\lambda_{max}$, | FWHM | CIE | | V | LE | EQE | PE | Lo, | RT$_{80\%}$ |
| Example | nm | nm | X | Y | (V) | (cd/A) | (%) | (lm/W) | nits | (h) |
| Ex. 1 | 510 | 70 | 0.290 | 0.622 | 5.7 | 48.7 | 14.2 | 26.7 | 14,486 | 76 |
| Ex. 2 | 512 | 68 | 0.282 | 0.629 | 5.2 | 51.6 | 14.9 | 31.2 | 16,186 | 67 |
| Ex. 3 | 527 | 76 | 0.349 | 0.610 | 6.1 | 54.1 | 14.9 | 28.1 | 15,179 | 204 |
| Ex. 4 | 527 | 75 | 0.350 | 0.611 | 5.6 | 54.3 | 15 | 30.2 | 15,810 | 220 |
| Ex. 5 | 522 | 68 | 0.329 | 0.623 | 5.4 | 66.6 | 18.2 | 38.6 | 18,557 | 174 |
| Ex. 6 | 526 | 72 | 0.342 | 0.616 | 4.9 | 66.5 | 18.1 | 42.7 | 19,885 | 184 |
| Comp. Ex. 1 | 527 | 72 | 0.341 | 0.617 | 6 | 55.6 | 15.2 | 29.1 | 16,066 | 165 |
| Comp. Ex. 2 | 527 | 79 | 0.344 | 0.614 | 6.4 | 56.7 | 15.6 | 27.6 | 15,436 | 155 |
| Comp. Ex. 3 | 507 | 68 | 0.294 | 0.615 | 5.8 | 44.2 | 13.1 | 23.9 | 13,930 | 14 |
| Comp. Ex. 4 | 522 | 66 | 0.328 | 0.624 | 5.5 | 65 | 17.8 | 37.3 | 18,170 | 116 |
| Comp. Ex. 5 | 526 | 72 | 0.340 | 0.616 | 5.1 | 65.3 | 17.9 | 40.4 | 19,740 | 128 |

From Device Examples 1-6, it can be seen that the CD$_3$ compounds provided herein as emitting dopants provide long lifetime. In particular, the lifetime, $RT_{80\%}$ (defined as the time required for the initial luminance, $L_0$, to decay to 80% of its value, at a constant current density of 40 mA/cd$^2$ at room temperature) of Device Examples containing the compounds provided are notably higher than Comparative Examples, which contain the corresponding CH$_3$ substituted compounds. Specifically, Compound 13 used in Device Examples 3 and 4 provided $RT_{80\%}$ of 204 h and 220 h, respectively, as compared to $RT_{80\%}$ of 165 h and 155 h for Comparative Examples 1 and 3, which used the corresponding CH$_3$ substituted compound (E1).

The data above also demonstrates that heteroleptic CD3 containing compounds provided herein may provide devices having improved lifetime and efficiency. In particular, Device Examples 5 and 6 containing Compound 27 provide better lifetime and efficiency than Comparative Examples 4 and 5, which contain the corresponding CH$_3$ substituted compound (E3). Specifically, Compound 27 provided $RT_{80\%}$ of 174 h and 184 h as compared to $RT_{80\%}$ of 116 h and 128 h for the corresponding methyl-substituted compound E3.

Additionally, the methyl-d3 substituted compounds provided devices with improved efficiency. In particular, Compounds 10, 13 and 27 achieved an operating voltage lower than that of the Comparative Examples using corresponding CH$_3$ substituted compounds. Specifically, Compounds 10, 13, and 27 provide an operating voltage (V) of 5.2 V, 5.6 V, and 4.9 V compared to 6.4 V, 5.8 V, and 5.1 V, respectively.

The data above suggests that the methyl-d3 substituted compounds provided herein can be excellent emitting dopants for phosphorescent OLEDs. These compounds provide devices with improved color, efficiency and lifetime.

As used herein, the following compounds have the following structures:

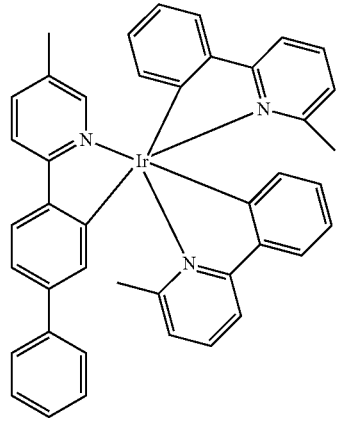

E4

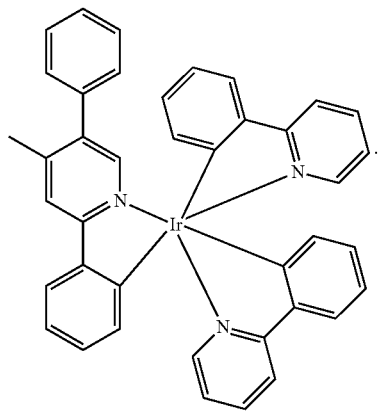

E5

TABLE 4

| Example | HIL | HTL | Host | A % | BL | ETL |
|---|---|---|---|---|---|---|
| Ex. 7 | E5 100 Å | NPD 300 Å | H1 | Cmpd 43 7% | H1 100 Å | Alq 400 Å |
| Ex. 8 | E5 100 Å | NPD 300 Å | H1 | Cmpd 43 10% | H1 100 Å | Alq 400 Å |
| Comp. Ex. 6 | E1 100 Å | NPD 300 Å | H1 | E4 7% | H1 100 Å | Alq 400 Å |
| Comp. Ex. 7 | E1 100 Å | NPD 300 Å | H1 | E4 10% | H1 100 Å | Alq 400 Å |

TABLE 5

| | $\lambda_{max}$, nm | FWHM nm | CIE X | CIE Y | V (V) | LE (cd/A) | EQE (%) | PE (lm/W) | At 40 mA/cm$^2$ Lo, nits | $RT_{80\%}$ (h) |
|---|---|---|---|---|---|---|---|---|---|---|
| Example | | | | | | | | | | |
| Ex. 7 | 534 | 62 | 0.368 | 0.604 | 6.1 | 63.3 | 17.2 | 32.7 | 14,037 | 374 |
| Ex. 8 | 534 | 64 | 0.380 | 0.597 | 5.3 | 69 | 18.8 | 40.7 | 18,702 | 365 |
| Comp. Ex. 6 | 534 | 64 | 0.380 | 0.596 | 5.7 | 68 | 18.6 | 37.3 | 17,776 | 212 |
| Comp. Ex. 7 | 534 | 64 | 0.380 | 0.597 | 5.3 | 68.8 | 18.8 | 40.5 | 19,306 | 283 |

As can be seen from Device Examples 7 and 8, Compound 43 has comparable efficiency and color against E4, and the device lifetime was much longer. Device Example 7 showed $LT_{80}$ of 374 h and Comparative Example 6 showed lifetime of 212 h. Device Example 8 showed $LT_{80}$ of 365 h and Comparative Example 7 showed lifetime of 283 h. The device data shows that the methyl-d3 substituted compounds provided may improve device lifetime.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising a ligand having the structure:

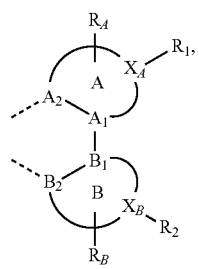

FORMULA I wherein A and B may independently represent a 6-membered aromatic ring;
wherein $A_1$ and $B_1$ are independently C or N;
wherein $A_2$ and $B_2$ is C, and one of $A_2$ and $B_2$ is N;
wherein $R_A$ and $R_B$ may represent mono, di, or tri substitutions;
wherein $X_A$ and $X_B$ are independently C or a heteroatom;
wherein $R_A$, $R_B$, $R_1$ and $R_2$ are independently selected from the group consisting of hydrogen, alkyl, alkoxy, amino, alkenyl, alkynyl, arylalkyl, aryl, and heteroaryl;
wherein at least one of $R_A$, $R_B$, $R_1$ and $R_2$ includes CD, $CD_2$ or $CD_3$, wherein the deuterium atoms are provided within an alkyl chain or at the end of an alkyl chain;
wherein $R_A$, $R_B$, $R_1$ and $R_2$ may be linked;
wherein $R_A$, $R_B$, $R_1$ and $R_2$ may be fused; and
wherein the ligand is coordinated to Ir.

2. The compound of claim 1, wherein at least one of substituents of $R_A$ and $R_B$ is $CD_3$ attached directly to ring A, ring B, or a ring that is conjugated or fused to ring A or ring B.

3. The compound of claim 1, wherein $X_A$ and $X_B$ are independently C or N and when $X_A$ is N, $R_1$ is aryl.

4. The compound of claim 1, wherein $X_A$ and $X_B$ are independently C or N and when $X_A$ is N, $R_1$ is phenyl further substituted with a group consisting of alkyl, alkoxy, amino, alkenyl, alkynyl, arylalkyl, aryl, and heteroaryl and wherein the group includes at least one of CD, $CD_2$ or $CD_3$.

5. The compound of claim 1, wherein the ligand is selected from the group consisting of:

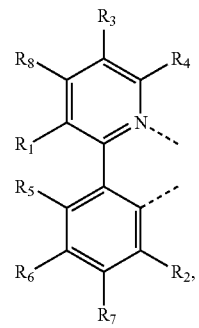

IV

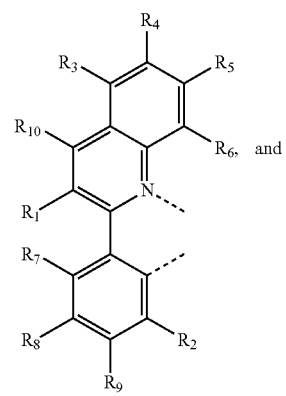

VI

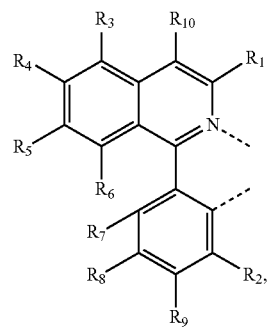

VII wherein $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylalkyl, aryl, and heteroaryl; and $R_1$, $R_2$, $R_3$, $R_4$, $R_5$, $R_6$, $R_7$, $R_8$, $R_9$, and $R_{10}$ may be linked;
wherein $R_1$, $R_2$, $R_3$, $R_4$, $R_5$, $R_6$, $R_7$, $R_8$, $R_9$, and $R_{10}$ may be fused; and
wherein at least one of $R_1$, $R_2$, $R_3$, $R_4$, $R_5$, $R_6$, $R_7$, $R_8$, $R_9$, and $R_{10}$ includes an alkyl group that includes CD, $CD_2$, or $CD_3$.

6. The compound of claim 5, wherein the ligand has the formula:

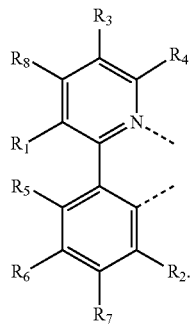

IV

7. The compound of claim 5, wherein the ligand has the formula:

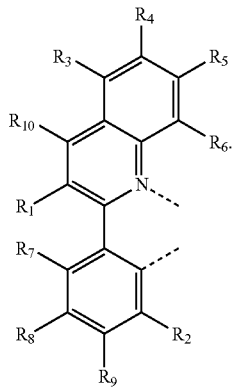

VI

8. The compound of claim 5, wherein the ligand has the formula:

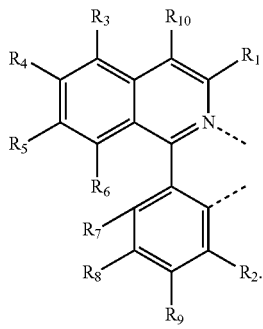

VII

9. The compound of claim 1, wherein A is selected from the group consisting of pyridine, pyridazine, pyrimidine, pyrazine, and triazine.

10. The compound of claim 1, wherein B is selected from the group consisting of benzene, pyridine.

11. The compound of claim 1, wherein the ligand having FORMULA I is a ligand in a homoleptic compound.

12. The compound of claim 1, wherein the ligand having FORMULA I is a ligand in a heteroleptic compound.

13. An organic light emitting device comprising:
an anode;
a cathode; and
an organic layer, disposed between the anode and the cathode, wherein the organic layer comprises a compound further comprising a ligand having the structure:

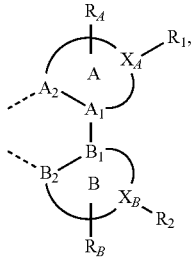

FORMULA I wherein A and B may independently represent a 6-membered aromatic ring;
wherein $A_1$ and $B_1$ are independently C or N;
wherein $A_2$ and $B_2$ is C, and one of $A_2$ and $B_2$ is N;
wherein $R_A$ and $R_B$ may represent mono, di, or tri substitutions;
wherein $X_A$ and $X_B$ are independently C or a heteroatom;
wherein $R_A$, $R_B$, $R_1$ and $R_2$ are independently selected from the group consisting of hydrogen, alkyl, alkoxy, amino, alkenyl, alkynyl, arylalkyl, aryl, and heteroaryl;
wherein at least one of $R_A$, $R_B$, $R_1$ and $R_2$ includes CD, $CD_2$ or $CD_3$, wherein the deuterium atoms are provided within an alkyl chain or at the end of an alkyl chain;
wherein $R_A$, $R_B$, $R_1$ and $R_2$ may be linked;
wherein $R_A$, $R_B$, $R_1$ and $R_2$ may be fused; and
wherein the ligand is coordinated to Ir.

14. The device of claim 13, wherein the ligand has the structure:

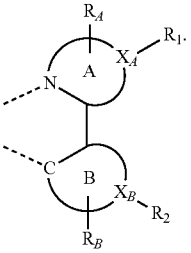

FORMULA Ia

15. The device of claim 14, wherein at least one of $R_A$, $R_B$, $R_1$ and $R_2$ is $CD_3$.

16. The device of claim 13, wherein at least one of the substituents of $R_A$ and $R_B$ is $CD_3$ attached directly to ring A, ring B, or a ring that is conjugated or fused to ring A or ring B.

17. The device of claim 13, wherein $X_A$ and $X_B$ are independently C or N and when $X_A$ is N, $R_1$ is aryl.

18. The device of claim 13, wherein $X_A$ and $X_B$ are independently C or N and when $X_A$ is N, $R_1$ is phenyl further substituted with a group consisting of alkyl, alkoxy, amino, alkenyl, alkynyl, arylalkyl, aryl, and heteroaryl and wherein the group includes at least one of CD, $CD_2$ or $CD_3$.

19. The device of claim 13, wherein the ligand is selected from the group consisting of:

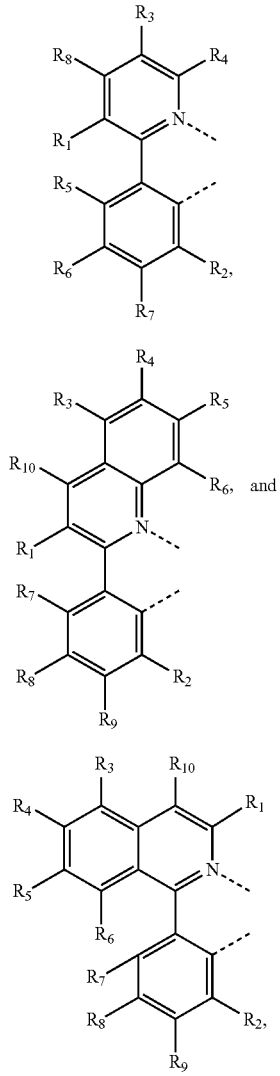

wherein $R_1$, $R_2$, $R_3$, $R_4$, $R_5$, $R_6$, $R_7$, $R_8$, $R_9$, and $R_{10}$ are independently selected from the group consisting of hydrogen, alkyl, alkoxy, amino, alkenyl, alkynyl, arylalkyl, aryl, and heteroaryl; and $R_1$, $R_2$, $R_3$, $R_4$, $R_5$, $R_6$, $R_7$, $R_8$, $R_9$, and $R_{10}$ may be linked;
wherein $R_1$, $R_2$, $R_3$, $R_4$, $R_5$, $R_6$, $R_7$, $R_8$, $R_9$, and $R_{10}$ may be fused; and
wherein at least one of $R_1$, $R_2$, $R_3$, $R_4$, $R_5$, $R_6$, $R_7$, $R_8$, $R_9$, and $R_{10}$ includes an alkyl group that includes CD, $CD_2$, or $CD_3$.

20. The device of claim 13, wherein A is selected from the group consisting of imidazole, pyridine, pyridazine, pyrimidine, pyrazine, and triazine.

21. The device of claim 13, wherein B is selected from the group consisting of benzene, pyridine.

22. The device of claim 13, wherein the organic layer is an emissive layer and the compound is an emitting dopant.

23. The device of claim 22, wherein the organic layer further comprises a host.

24. The device of claim 23, wherein the host has the formula:

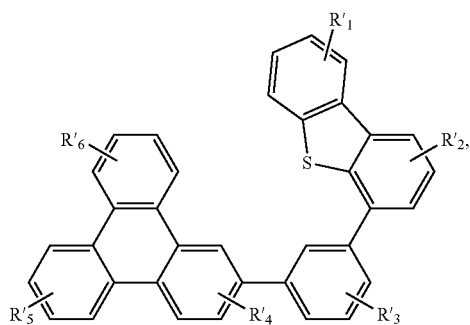

wherein $R'_1$, $R'_3$, $R'_5$, and $R'_6$ may represent mono, di, tri, or tetra substitutions;
wherein $R'_2$ and $R'_4$ may represent mono, di, or tri substitutions; and
wherein each of $R'_1$, $R'_2$, $R'_3$, $R'_4$, $R'_5$, and $R'_6$ is independently selected from the group consisting of hydrogen, alkyl and aryl.

25. The device of claim 23, wherein the host is

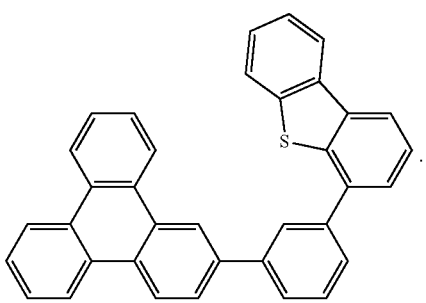

26. A consumer product comprising a device, the device comprising:
 an anode;
 a cathode; and
 an organic layer, disposed between the anode and the cathode, wherein the organic layer comprises a compound comprising a ligand having the structure:

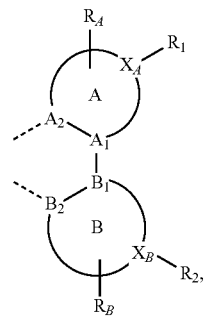

FORMULA I wherein A and B may independently represent a 6-membered aromatic ring;
wherein $A_1$ and $B_1$ are independently C or N;
wherein $A_2$ and $B_2$ are independently C, and one of $A_2$ and $B_2$ is N;
wherein $R_A$ and $R_B$ may represent mono, di, or tri substitutions;

wherein $X_A$ and $X_B$ are independently C or a heteroatom;

wherein $R_A$, $R_B$, $R_1$ and $R_2$ are independently selected from the group consisting of hydrogen, alkyl, alkoxy, amino, alkenyl, alkynyl, arylalkyl, aryl, and heteroaryl;

wherein at least one of $R_A$, $R_B$, $R_1$ and $R_2$ includes CD, $CD_2$ or $CD_3$, whereby the deuterium atoms are provided within an alkyl chain or at the end of an alkyl chain;

wherein $R_A$, $R_B$, $R_1$ and $R_2$ may be linked;

wherein $R_A$, $R_B$, $R_1$ and $R_2$ may be fused; and wherein the ligand is coordinated to Ir.

* * * * *

UNITED STATES PATENT AND TRADEMARK OFFICE
CERTIFICATE OF CORRECTION

PATENT NO. : 9,634,265 B2
APPLICATION NO. : 13/960264
DATED : April 25, 2017
INVENTOR(S) : Chuanjun Xia, James Fiordeliso and Raymond Kwong Page 1 of 1

It is certified that error appears in the above-identified patent and that said Letters Patent is hereby corrected as shown below:

In the Claims

In Claim 1, Column 99, Line 41, following the word wherein please insert -- one of --.

In Claim 13, Column 102, Line 24, following the word wherein please insert -- one of --.

In Claim 26, Column 104, Line 64, please delete "wherein $A_2$ and $B_2$ are independently" and insert -- wherein one of $A_2$ and $B_2$ is --.

Signed and Sealed this
Fourth Day of September, 2018

Andrei Iancu
*Director of the United States Patent and Trademark Office*